United States Patent [19]
McIver et al.

[11] Patent Number: 6,066,673
[45] Date of Patent: May 23, 2000

[54] ENZYME INHIBITORS

[75] Inventors: John McMillan McIver; Todd Laurence Underiner; Timothy Bates, all of Cincinnati, Ohio

[73] Assignee: The Procter & Gamble Company, Cincinnati, Ohio

[21] Appl. No.: 09/041,196

[22] Filed: Mar. 12, 1998

[51] Int. Cl.[7] .................. A61K 31/155; C07C 277/08
[52] U.S. Cl. ................... 514/634; 514/844; 514/846; 564/230; 564/238
[58] Field of Search ................ 424/401; 514/844, 514/846, 865, 634; 564/238, 230, 240

[56] References Cited

U.S. PATENT DOCUMENTS

| | | | |
|---|---|---|---|
| 4,021,472 | 5/1977 | Fujii et al. | 260/472 |
| 4,179,337 | 12/1979 | Davis et al. | 435/181 |
| 4,224,342 | 9/1980 | Fujii et al. | 424/310 |
| 4,310,533 | 1/1982 | Uegai et al. | 424/267 |
| 4,454,338 | 6/1984 | Fujii et al. | 560/34 |
| 4,556,560 | 12/1985 | Buckingham | 424/145 |
| 4,570,006 | 2/1986 | Fujii et al. | 549/442 |
| 4,745,161 | 5/1988 | Saudek et al. | 525/420 |
| 4,746,737 | 5/1988 | Fujii et al. | 540/575 |
| 4,873,253 | 10/1989 | Okamoto et al. | 514/352 |
| 4,948,891 | 8/1990 | Schnur et al. | 544/329 |
| 5,037,883 | 8/1991 | Kopecek et al. | 525/54.1 |
| 5,075,335 | 12/1991 | Souda et al. | 514/535 |
| 5,091,193 | 2/1992 | Enjoiras et al. | 424/642 |
| 5,162,307 | 11/1992 | Digenis et al. | 514/19 |
| 5,183,660 | 2/1993 | Ikeda et al. | 424/94.3 |
| 5,352,704 | 10/1994 | Okuyama et al. | 514/619 |
| 5,372,807 | 12/1994 | Poiani et al. | 424/78.36 |
| 5,376,655 | 12/1994 | Imaki et al. | 514/237.5 |
| 5,446,090 | 8/1995 | Harris | 525/54.1 |
| 5,455,027 | 10/1995 | Zalipsky et al. | 424/78.17 |
| 5,571,844 | 11/1996 | Stuber et al. | 514/602 |
| 5,622,984 | 4/1997 | Nakai et al. | 514/423 |
| 5,643,575 | 7/1997 | Martinez et al. | 424/194.1 |
| 5,648,506 | 7/1997 | Desai et al. | 549/510 |
| 5,660,822 | 8/1997 | Poiani et al. | 424/78.17 |
| 5,723,133 | 3/1998 | Nagai et al. | 424/401 |
| 5,783,178 | 7/1998 | Kabanov et al. | 424/78.31 |
| 5,840,485 | 11/1998 | Lebl et al. | 435/6 |

FOREIGN PATENT DOCUMENTS

| | | |
|---|---|---|
| 435 235 B1 | 12/1990 | European Pat. Off. . |
| 452 179 A2 | 3/1991 | European Pat. Off. . |
| 486 702 A1 | 6/1991 | European Pat. Off. . |
| 584 876 A2 | 8/1993 | European Pat. Off. . |
| 673 924 A1 | 12/1993 | European Pat. Off. . |
| 2252351 | 11/1973 | France . |
| WO 93/15189 | 8/1993 | WIPO . |
| 93/25212 | 12/1993 | WIPO . |
| 94/27641 | 12/1994 | WIPO . |
| 94/28024 | 12/1994 | WIPO . |
| 95/06058 | 3/1995 | WIPO . |
| 97/25067 | 7/1997 | WIPO . |
| 97/38735 | 10/1997 | WIPO . |

OTHER PUBLICATIONS

Bernkop–Schnurch,m et al., "Synthesis and In Vitro Evaluation of Chitosan–EDTA–Protease Inhibitor Conjugates Which Might Be Useful in Oral Delivery of Peptides and Proteins", *Pharmaceutical Research*, vol. 15, No. 2, pp. 263–269 (1998).

Noguchi, H., Iwata, H., Ikada, Y., "Synthesis of Monomeric and Polymeric Conjugates Carrying a Thrombin Inhibitor Through an Ester Bond", J. Biomed Mater Res, vol. 39, pp. 621–629 (1998).

Domb, A.J., Cravalho, E.G., Langer, R., "The Synthesis of Poly(hydroxamic Acid) from Poly(acrylamide)", Journal of Polymer Science; Part A, vol. 26, pp. 2623–2630 (1988).

Subr, V., Duncan, R., Hanada, K., Cable, H.C., Kopecek, J., "A Lysosomotropic Polymeric Inhibitor of Cysteine Proteinases", Journal of Controlled Release, vol. 4, pp. 63–68 (1986).

Rypacek, F., "Polymer–Bound Enzyme Inhibitors: Synthesis, Properties, and Physiological Relevance", Critical Reviews in Therapeutic Drug Carrier Systems, vol. 9(3,4), pp. 189–212 (1992).

Macfarlane, G.T., Cummings, J.H., Allison, "Protein Degradation by Human Intestinal Bacteria", Journal of General Microbiology, vol. 132, pp. 1647–1656 (1986).

Takerkart, G., Segard, E., Monsigny, M., "Preparation and Properites of Organophilic Trypsin Macro–Inhibitors: Diamidino–α, ω–Diphenylcarbamyl–Poly(Ethylene Glycol)", FEBS Letters, vol. 42, No. 2, pp. 214–217 (1974).

Andersen, P.H., Bucher, A.P., Saeed, I., Lee, P.C., Davis, J.A., Maibach, H.I., "Faecal Enzymes: In Vivo Human Skin Irritation", Contact Dermatitis, vol. 30, pp. 152–158 (1994).

Buckingham, K.W., Berg, R.W., "Etiologic Factors in Diaper Dermatitis: The Role of Feces", Pediatric Dermatology, vol. 3, No. 2, pp. 107–112 (1986).

Berg, R.W., Buckingham, K.W., Stewart, R.L., "Etiologic Factors in Diaper Dermatitis: The Role of Urine", Pediatric Dermatology, vol. 3, No. 2, pp. 102–106 (1986).

Hans–Hartwig, O., Schirmeister, T., "Cysteine Proteases and Their Inhibitors", Chem Rev., vol. 97, pp. 133–171 (1997).

(List continued on next page.)

*Primary Examiner*—Sreeni Padmanabhan
*Attorney, Agent, or Firm*—Richard S. Echler, Sr.; Kelly L. McDow-Dunham; Bart S. Hersko

[57] ABSTRACT

The present invention relates to compounds, compositions, and methods which are useful for the prevention and treatment of adverse health, skin, hair, and oral conditions. The compounds, compositions, and methods are also widely applicable for use in health, skin, hair, oral, beauty, and personal care applications.

In particular, the present invention relates to compounds having the structure:

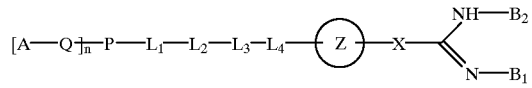

and the tautomers, acceptable salts, and biohydrolyzable amides, esters, and imides thereof, wherein A, Q, n, P, $L_1$, $L_2$, $L_3$, $L_4$, Z, X, $B_1$, and $B_2$ are defined herein.

22 Claims, No Drawings

OTHER PUBLICATIONS

Bernkop–Schnurch, A., Apprich, I., "Synthesis and Evaluation of a Modified Mucoadhesive Polymer Protecting from α–chymotrypsinic Degradation", International Journal of Pharmaceuticals, vol. 146, pp. 247–254 (1997).

Bernkop–Schnurch, A. Gockel, N.C., "Development and Analysis of a Polymer Protecting from Luminal Enzymatic Degradation Caused by α–Chymotrypsin", Drug Development and Industrial Pharmacy, vol. 23, No. 8, pp. 733–740 (1997).

Bernkop–Schnurch, A., Bratengeyer, I., Valenta, C., "Development and In Vitro Evaluation of a Drug Delivery System Protecting from Trypsinic Degradation", International Journal of Pharmaceutics, vol. 157, pp. 17–25 (1997).

Zalipsky, S., Gilon, C., Zilkha, A., Attachment of Drugs to Polyethylene Glycols, Eur. Polym. J., vol. 19, No. 12, pp. 1177–1193 (1983).

ENZYME INHIBITORS

FIELD OF THE INVENTION

The compounds, compositions, and methods of the present invention are widely useful in health, skin, hair, oral, beauty, and personal care applications. In addition, the present compounds, compositions, and methods are useful for laundry and cleaning, hard surface cleaning, lawn and garden, and coatings applications wherein enzyme inhibition may provide a benefit for the consumer.

BACKGROUND OF THE INVENTION

The present invention relates to compounds having inhibitory activity against enzymes which have been implicated in the promotion of certain adverse health, skin, hair, and oral conditions. Such enzymes include, but are not limited to lipases, serine proteases, metalloproteases, cysteine proteases, and aspartic proteases. More specifically these enzymes include, for example, lipase, carboxypeptidase A, chymotrypsin, elastase, trypsin, and leucine aminopeptidase. The compounds are useful against a wide spectrum of conditions, including but not limited to, diaper rash, acne, periodontal disease, and obesity. The compounds also have utility as contraceptives and drug delivery systems.

Diaper rash is a common form of irritation and inflammation of those diapered areas of an infant's body. This condition is also referred to as diaper dermatitis, napkin dermatitis, napkin rash, and nappy rash. While certainly more common in infants, this condition is not limited to infants. Any individual who suffers from incontinence to the extent that the use of absorbent articles is required may develop this condition. Such individuals include newborns, the elderly, and those who are critically ill or are nonambulatory.

Diaper rash is a condition which, in its earliest stage, is a contact irritant dermatitis. The irritation of simple diaper rash results from the extended contact of skin with urine, feces, or both. While it is known that body waste contributes to the promotion of diaper rash, the precise component or components of the urine or feces responsible for the resulting irritation of the skin have not been conclusively identified. Among the most commonly accepted factors linked to diaper rash are ammonia, fecal enzymes, bacteria, the products of bacterial action, urine pH, overhydration, and *Candida albicans*.

There is significant evidence that fecal proteolytic and lipolytic enzymes are important in the onset of the skin irritation and inflammation resulting from such conditions as, for example, diaper rash. See, e.g., Buckingham, U.S. Pat. No. 4,556,560, 1985; Zimmerer, U.S. Pat. No. 4,657, 537, 1987; Berg et al., U.S. Pat. No. 4,685,909, 1987; Jordan et al., U.S. Pat. No. 4,842,593, 1989; Buckingham et al., "Etiologic Factors in Diaper Dermatitis: The Role of Feces", *Pediatric Dermatology*, Vol. 3, pp. 107–112 (1986); and Anderson et al., "Fecal Enzymes: in vivo Human Skin Irritation", *Contact Dermatitis*, Vol. 30, pp. 152–158 (1994). Furthermore, these effects are likely promulgated if urine is present and or if the skin is occluded.

McFarlane et al., "Contribution of the Microflora to Proteolysis in the Human Large Intestine", *Journal of Applied Bacteriology*, Vol. 64 (1988) pp. 37–46, report that fecal microflora contribute significantly to the proteolytic activity of human feces, which suggests that a wide number of bacterial enzymes, including proteases, lipases and other esterases, may contribute to skin damage. Studies with inhibitors designed to inhibit the enzymatic activity of various classes of proteases showed that serine proteases, cysteine proteases, and metalloproteases were the most likely to be responsible for the overall proteolytic activity of feces. However, the relative contributions of the different types of proteolytic enzymes to skin damage remains largely unknown.

Currently, several intervention approaches designed to prevent or treat such skin conditions as diaper rash attempt to address multiple causes or important cofactors. Reducing skin hydration by frequent changing of diapers, moisture absorbing powders, superabsorbent materials, and improving air flow in diapers are well known approaches. The use of artificial barriers is also widely practiced. Typical is the use of a cream, ointment, lotion, or paste which provides some degree of protection against fecal or urine irritants, regardless of their specific nature. However, the barrier approach, while reducing access of irritants to the skin may be occlusive in itself and can be aesthetically unpleasing.

Although there appear to be multiple factors involved in the development of such conditions as diaper rash, it is likely that the physiological responses of the skin to the irritants, although complicated, may involve some common mechanisms. For example, it has been shown that the production of cytokines by skin cells is a common response to the presence of irritants or skin barrier (stratum corneum) perturbation. The principal cell type that appears to be involved in the production of cytokines is the keratinocyte, which is the cell type found directly beneath the stratum corneum and is the most likely to initially encounter an irritant. It has been demonstrated that the keratinocyte secretes a wide variety of different cytokines in response to irritants, including the proinflammatory cytokine interleukin 1-alpha (IL-1$\alpha$). This cytokine, and others, induce a cascade of events which may eventually lead to the physiological appearance of erythema, papules, scaling, and ulceration, which are collectively described as diaper rash.

While certain compositions have been previously described for the treatment of diaper rash that include inhibitors of fecal urease, lipase and/or protease enzyme activity, the importance of a proactive regimen to prevent the initial cytokine response by keratinocytes leading to the inflammatory cascade has not been previously recognized. In particular, it has not been previously recognized that fecal enzymes play an important role in inducing the cytokine response of keratinocytes to irritants, and that inhibition of fecal enzymes provides a more specific means of preventing or treating diaper rash than has been previously disclosed.

The compounds, compositions, and methods of the present invention overcome the foregoing deficiencies by inhibiting enzymes which are, as described supra, implicated in the causation of such conditions as, for example, the skin damage and inflammation of diaper rash. The inventors herein have surprisingly discovered that the compounds of the present invention inhibit enzymes which have been implicated in the cause of such conditions as diaper rash. It has been discovered that the present compounds have inhibitory activity against proteolytic and/or lipolytic enzymes, including, but not limited to, lipase, carboxypeptidase A, chymotrypsin, elastase, trypsin, and/or leucine aminopeptidase. The present compounds inhibit these enzymes which reduces the irritant potential of the fecal agent.

Furthermore, the inventors have surprisingly discovered that the compounds of the present invention have limited absorption through skin, thereby greatly reducing potential systemic side effects. Accordingly, such compounds may be delivered topically to the skin through such delivery systems as, for example, the topsheet of a diaper, which enables the close proximity of the compounds with the skin.

Furthermore, the present inventors have discovered that the utility of the present compounds is not limited to the treatment and prevention of such conditions as diaper rash. The present compounds may also be useful in the treatment of obesity, acting by partial inhibition of lipase in the intestine. Therefore, the present compounds, due to their inhibitory activity and polymerically conjugated nature, may be particularly safe in this regard due to their limited absorption following oral ingestion.

The present compounds are also useful for the treatment of skin against such inflammatory conditions as, for example, acne. Without intending to be limited by theory, bacterial lipases break down triglycerides in the sebum to form free fatty acids which are known to irritate the follicular wall. The lipase inhibiting power of the present compounds prevents oil production and tissue irritation. Furthermore, inhibition of bacterial proteases by the compounds of the present invention also reduce irritation in the inflamed follicle because these compounds comprise a poly (alkylene oxide) moiety which facilitates penetration into the sebum.

While certain non-polymeric guanidine and amidine derivatives have been described as inhibitors of proteases, including trypsin, chymotrypsin, plasmin, kallikrein, thrombin, and acrosin, the compounds of the present invention have not been described in the literature. See. e.g., U.S. Pat. No. 5,622,984, Nakai et al.; European Patent Application 0,486,702, Kabushiki et al., 1992; U.S. Pat. No. 4,948, 891, Schnur et al., 1990; and U.S. Pat. No. 4,454,338, Fujii et al., 1984. However, while the art is replete with such guanidino and amidino enzyme inhibitors, there appears to be no mention of the use of such inhibitors for the alleviation or prevention of diaper rash.

Moreover, while the conjugation of polymers with peptides, polypeptides, and certain small molecules is known, such conjugation has been achieved for widely varying purposes. For example, copolymers of amino acid residues or peptide sequences with poly(alkylene oxides) wherein the copolymer is conjugated with pharmaceutically active compounds has been described. Such conjugates are disclosed as being useful for enhancing the functionality of poly(alkylene oxides). See U.S. Pat. No. 5,455,027, Zalipsky et al., 1995. Another example is the conjugation of taxol with polymers, particularly poly(ethylene oxide). In this instance, conjugation is utilized to increase the water-solubility, and thus delivery, of the drug. The taxol moiety is ultimately hydrolyzed from an implanted gel containing the conjugate. See U.S. Pat. No. 5,648,506, Desai et al., 1997. As a further example, poly(ethylene oxide) conjugates of para-aminobenzamidine have been prepared for the purification of enzymes by affinity extraction. French Patent Application No. 2,252,351, Segard et al., 1973; and Takerkart, G., "Preparation and Properties of Organophilic Trypsin Macro-Inhibitors: Diamidino-α, ω-Diphenylcarbamyl-Poly(Ethylene Glycol)", *FEBS Letters*, Vol. 42 pp. 214–217 (1974). See also, U.S. Pat. No. 5,162,307, Digenis et al., 1992; Bernkop-Schnurch et al., "Synthesis and Evaluation of a Modified Mucoadhesive Polymer Protecting from α-Chymotrypsinic Degradation", *International Journal of Pharmaceutics*, Vol. 146, pp. 247–254 (1997); Bernkop-Schnurch et al., "Development and Analysis of a Polymer Protecting from Luminal Enzymatic Degradation Caused by α-Chymotrypsin", *Drug Development and Industrial Pharmacy*, Vol. 23, pp. 733–740 (1997); and Bernkop-Schnurch et al., "Development and in vitro Evaluation of a Drug Delivery System Protecting from Trypsinic Degradation", *International Journal of Pharmaceutics*, Vol. 157, pp. 17–25 (1997).

Accordingly, the present inventors have surprisingly discovered that the compounds, compositions, and methods herein have broad-spectrum applicability and enzymatic activity, particularly against conditions wherein proteases and lipases have been implicated.

SUMMARY OF THE INVENTION

The present invention provides compounds, compositions, and methods which are useful for the prevention and treatment of adverse health, skin, hair, and oral conditions. The compounds, compositions, and methods are also widely applicable for use in health, skin, hair, oral, beauty, and personal care applications.

In particular, the present invention relates to compounds having the structure:

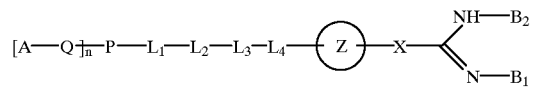

and the tautomers, acceptable salts, and biohydrolyzable amides, esters, and imides thereof, wherein:

(a) $B_1$ is selected from the group consisting of hydrogen, methyl, ethyl, propyl, a methylene group connected to $B_2$ through a single bond such that $B_1$ and $B_2$ form a five-membered ring, and a methylene group connected to $B_2$ through another methylene group such that $B_1$ and $B_2$ form a six-membered ring;

(b) $B_2$ is selected from the group consisting of hydrogen, methyl, ethyl, propyl, a methylene group connected to $B_1$ through a single bond such that $B_1$ and $B_2$ form a five-membered ring, and a methylene group connected to $B_1$ through another methylene group such that $B_1$ and $B_2$ form a six-membered ring;

(c) X is selected from the group consisting of nil, —$CH_2$—, and —NH—;

(d) Z is an aromatic, substituted or unsubstituted, monocyclic or polycyclic, carbocyclic ring or heterocyclic ring;

(e) $L_1$, $L_2$, and $L_3$ are each, independently, selected from the group consisting of nil, —NH—, —O—, —S—, —C(O)—, —$CF_2$—, alkyl, alkenyl, cycloalkyl, aryl, arylalkyl, arylalkenyl, —C(O)NH—, —NH—$SO_2$— $R^1$—, —C(O)—$R^2$—, —C(O)—$R^3$—O—, —C(O)— $R^4$—S—, —C(O)—$R^5$—NH—, —NH—$R^6$—, —O—$R^7$—, —C(O)O—$R^8$—, —C(O)NH—$R^9$—, —NHC(O)—$R^{10}$, —OC(O)$R^{11}$, and —C(O)—CH ($R^{12}$)—N($R^{13}$)—Y—, wherein $R^1$, $R^2$, $R^3$, $R^4$, $R^5$, $R^6$, $R^7$, $R^8$, $R^9$, $R^{10}$, and $R^{11}$ are, independently, selected from the group consisting of alkyl, alkenyl, cycloalkyl, aryl, arylalkyl, arylalkenyl, alkylamino, protected alkylamrino, arylamino, protected arylamino, arylalkylamino, protected arylalkylamino, wherein $R^{12}$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{13}$ is hydrogen, or $R^{12}$ and $R^{13}$ together form a monocyclic or polycyclic heterocyclic ring including the nitrogen to which $R^{13}$ is bonded, and wherein Y is nil or —C(O)—CH($R^{14}$)—N($R^{15}$)— wherein $R^{14}$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{15}$ is hydrogen, or $R^{14}$ and $R^{15}$ together form a second monocyclic or polycyclic heterocyclic ring including the nitrogen to which $R^{15}$ is bonded;

(f) $L_4$ is nil or —C(O)—;

(g) P is a poly(alkylene oxide) polymer selected from the group consisting of a linear poly(alkylene oxide), a branched chain poly(alkylene oxide), and a star poly (alkylene oxide);

(h) n is an integer from about 1 to about 100;

(i) Q is nil or —O—; and (j) A is selected from the group consisting of nil, alkyl, alkenyl, cycloalkyl, aryl, arylalkyl, arylalkenyl, Z', wherein Z' is a saturated, unsaturated or aromatic, monocyclic or polycyclic, carbocyclic ring or heterocyclic ring, —C(O)—Z', and

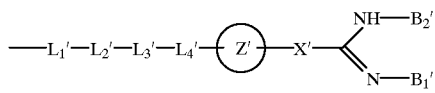

wherein $L_1'$, $L_2'$, $L_3'$, Z', X', $B_1'$, and $B_2'$ are defined as for, respectively, $L_1$, $L_2$, $L_3$, Z, X, $B_1$ and $B_2$;

wherein the compound is not (I) wherein (I) has the structure:

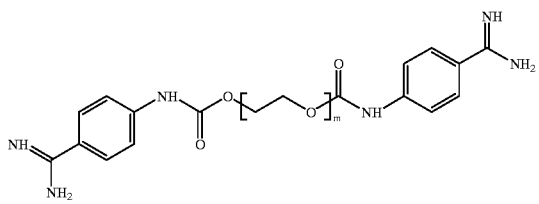

wherein m is an integer from about 3 to about 500.

The compounds of the present invention also include the optical isomers, diastereomers, enantiomers, tautomers, acceptable salts, and the biohydrolyzable amides, esters, and imides thereof.

These compounds have the ability to inhibit at least one enzyme, more preferably a protease or lipase, and particularly those which are responsible for the promotion of such conditions as, for example, diaper rash.

DETAILED DESCRIPTION OF THE INVENTION

The present invention relates to compounds having inhibitory activity against enzymes which have been implicated in the promotion of, for example, certain adverse health, skin, hair, and oral conditions. Such enzymes include, but are not limited to lipases, serine proteases, metalloproteases, cysteine proteases, and aspartic proteases. More specifically, such enzymes include lipase, carboxypeptidase A, chymotrypsin, elastase, trypsin, and leucine aminopeptidase.

The compounds of the present invention may also be used as intermediates for the preparation of other enzyme inhibitors. That is, the compositions may be further reacted, using known chemistry, to yield other active analogs.

As defined infra and as used herein, substituent groups may themselves be substituted. Such substitution may be with one or more substituents. Such substituents include those listed in Hansch, C. and A. Leo, *Substituent Constants for Correlation Analysis in Chemistry and Biology* (1979). Preferred substituents include, for example, alkyl, alkenyl, alkoxy, hydroxy, oxo, nitro, amino, alkylamino, cyano, halo, carboxy, alkoxyacyl (e.g., carboethyoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Publications and patents are referred to throughout this disclosure. All references cited herein are hereby incorporated by reference.

All percentages, ratios, and proportions used herein are by weight unless otherwise specified.

Definition and Usage of Terms

The following is a list of definitions for terms used herein:

As used herein "acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987. Preferred cationic salts include the alkali metal salts (such as, for example, sodium and potassium), alkaline earth metal salts (such as, for example, magnesium and calcium), and organic salts. Preferred anionic salts include the halides (such as, for example, chloride salts). Such acceptable salts must, of course, be appropriate for mammalian use.

As used herein, "alkenyl" is an unsubstituted or substituted hydrocarbon chain radical having from 2 to about 15 carbon atoms; preferably from 2 to about 10 carbon atoms; and more preferably from 2 to about 8 carbon atoms. Alkenyls have at least one olefinic double bond. Non-limiting examples of alkenyls include vinyl, allyl, and butenyl.

As used herein, "alkyl" is an unsubstituted or substituted saturated hydrocarbon chain radical having from 1 to about 15 carbon atoms; preferably from 1 to about 10 carbon atoms; more preferably from 1 to about 6 carbon atoms; and most preferably from 1 to about 4 carbon atoms. Preferred alkyl groups include, for example, methyl, ethyl, propyl, iso-propyl, and butyl.

As used herein, "alkylamino" may be an amino radical having one (secondary amine) or two (tertiary amine) alkyl substituents. Non-limiting examples of this type of alkylamino include methylamino (—NHCH$_3$), dimethylamino (—N(CH$_3$)$_2$), and methylethylamino (—N(CH$_3$)CH$_2$CH$_3$). An alkylamino may also be an alkyl radical bearing an amine functionality. Non-limiting examples of this type of alkylamino include —CH$_2$CH$_2$CH$_2$NH$_2$ or CH$_2$CH$_2$NH$_2$. Alkylaminos may be substituted or unsubstituted.

As used herein, "alkylene" refers to an alkyl, alkenyl, or alkynyl which is a diradical. For example, "methylene" is —CH$_2$—.

As used herein, "amino acid side chain" is the R moiety of a natural or unnatural amino acid having the structure:

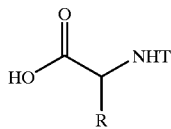

wherein T is hydrogen or is bonded to R to form a ring (as in, for example, the amino acid proline). Such amino acid side chains may be substituted or unsubstituted, and may be in D configuration, L configuration, or be racemic.

As used herein, "aryl" is an aromatic, carbocyclic or heterocyclic ring radical. Preferred aryl groups include, for example, phenyl, tolyl, xylyl, cumenyl, naphtyl, biphenyl, thienyl, furyl, pyrrolyl, pyridinyl, pyrazinyl, thiazolyl, pyrimidinyl, quinolinyl, tetrazolyl, benzothiazolyl, benzofuiryl, indolyl, and the like. Such aryls may be substituted or unsubstituted.

As used herein, "arylalkenyl" is an alkenyl radical substituted with an aryl group or an aryl radical substituted with an alkenyl group. Such arylalkenyls may be substituted or unsubstituted.

As used herein, "arylalkyl" is an alkyl radical substituted with an aryl group or an aryl radical substituted with an alkyl group. Preferred arylalkyl groups include benzyl, phenylethyl, and phenylpropyl. Arylalkyls may be substituted or unsubstituted.

As used herein, "arylalkylamino" may be an amine radical substituted with an arylalkyl group (e.g., —NH-benzyl). An arylalkylamino may also be an arylalkyl radical substituted with an amine group. Such arylalkylaminos may be substituted or unsubstituted.

As used herein, "arylamino" may be an amine radical substituted with an aryl group (e.g., —NH-aryl). An arylamino may also be an aryl radical substituted with an amine group (e.g., -aryl-$NH_2$). Arylaminos may be substituted or unsubstituted.

As used herein, "biohydrolyzable amides" are amides of the compositions of the present invention which do not interfere with the inhibitory activity of the compound, or that are readily converted in vivo by a mammalian subject to yield an active inhibitor.

As used herein, "biohydrolyzable esters" are esters of the compositions of the present invention which do not interfere with the inhibitory activity of the compound, or that are readily converted in vivo by a mammalian subject to yield an active inhibitor.

As used herein, "biohydrolyzable imides" are imides of the compositions of the present invention which do not interfere with the inhibitory activity of the compound, or that are readily converted in vivo by a mammalian subject to yield an active inhibitor.

As used herein, "carbocyclic ring" is a hydrocarbon ring radical. Carbocyclic rings are monocyclic or are fused, bridged, or spiro polycyclic rings. Monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms.

As used herein, "cycloalkyl" is a saturated carbocyclic or heterocyclic ring radical. Preferred cycloalkyl groups include, for example, cyclobutyl, cyclopentyl, and cyclohexyl.

As used herein, "heterocyclic ring" is a ring radical comprised of carbon atoms and one or more heteroatoms in the ring wherein the heteroatoms are selected from the group consisting of oxygen, sulfur, nitrogen, and phosphorous, more preferably, oxygen, sulfur, and nitrogen. Heterocyclic rings are monocyclic or are fused, bridged, or spiro polycyclic rings. Monocyclic rings contain from 3 to about 9 atoms, preferably from about 4 to about 7 atoms, and most preferably 5 or 6 atoms. Polycyclic rings contain from about 7 to about 17 atoms, preferably from about 7 to about 14 atoms, and most preferably 9 or 10 atoms.

As used herein, a "lower" hydrocarbon moiety (e.g., "lower" alkyl) is an alkyl having 1 to about 6, preferably 1 to about 4, carbon atoms.

As used herein, "protected alkylamino" is an alkylamino group wherein the amine functionality is substituted with a protecting group such as those disclosed in T. Greene, *Protecting Groups in Organic Synthesis*, John Wiley & Sons, 1981. Preferred protecting groups include N-tert-butoxycarbonyl (BOC) and N-benzyloxycarbonyl (CBZ).

As used herein, "protected arylamino" is an arylamino group wherein the amine functionality is substituted with a protecting group such as those disclosed in T. Greene, *Protecting Groups in Organic Synthesis*, John Wiley & Sons, 1981. Preferred protecting groups include N-tert-butoxycarbonyl (BOC) and N-benzyloxycarbonyl (CBZ).

As used herein, "protected arylalkylamino" is an arylalkylamino group wherein the amine functionality is substituted with a protecting group such as those disclosed in T. Greene, *Protecting Groups in Organic Synthesis*, John Wiley & Sons, 1981. Preferred protecting groups include N-tert-butoxycarbonyl (BOC) and N-benzyloxycarbonyl (CBZ).

As used herein, "safe and effective amount of a compound" (or other composition) means an amount that is effective to inhibit one or more enzymes at the site(s) of activity in a mammalian subject, without undue adverse side effects (such as toxicity, irritation, or allergic response), commensurate with a reasonable benefit/risk ratio when used in the manner of this invention.

As used herein, certain depictions of compounds or portions of compounds will be given. In the generic structure:

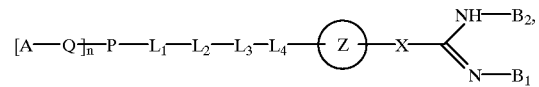

and similar structures,

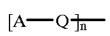

does not represent a repeating monomer unit because "A" only has one bond attached to it. Rather, this structure represents the number of "A—Q—" groups attached to the polymer, at different functionalization points of the polymer. For example, when n=3, the generic structure may also be represented as follows:

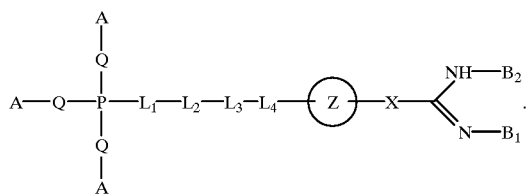

Compounds of the Present Invention

The compounds of the present invention are inhibitors of, for example, proteolytic and lipolytic enzymes. Such enzymes include, but are not limited to, lipases, serine proteases, metalloproteases, cysteine proteases, and aspartic proteases.

The compounds of the present invention are described in the Summary of the Invention. In particular, the present invention relates to compounds having the structure:

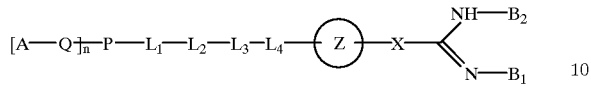

and the tautomers, acceptable salts, and biohydrolyzable amides, esters, and imides thereof, wherein:

(a) $B_1$ is selected from the group consisting of hydrogen, methyl, ethyl, propyl, a methylene group connected to $B_2$ through a single bond such that $B_1$ and $B_2$ form a five-membered ring, and a methylene group connected to $B_2$ through another methylene group such that $B_1$ and $B_2$ form a six-membered ring; more preferably, $B_1$ is hydrogen, a methylene group connected to $B_2$ through a single bond such that $B_1$ and $B_2$ form a five-membered ring, or a methylene group connected to $B_2$ through another methylene group such that $B_1$ and $B_2$ form a six-membered ring; even more preferably, $B_1$ is hydrogen or a methylene group connected to $B_2$ through a single bond such that $B_1$ and $B_2$ form a five-membered ring; $B_1$ is most preferably hydrogen;

(b) $B_2$ is selected from the group consisting of hydrogen, methyl, ethyl, propyl, a methylene group connected to $B_1$ through a single bond such that $B_1$ and $B_2$ form a five-membered ring, and a methylene group connected to $B_1$ through another methylene group such that $B_1$ and $B_2$ form a six-membered ring; more preferably, $B_2$ is hydrogen a methylene group connected to $B_1$ through a single bond such that $B_1$ and $B_2$ form a five-membered ring, or a methylene group connected to $B_1$ through another methylene group such that $B_1$ and $B_2$ form a six-membered ring; even more preferably, $B_2$ is hydrogen or a methylene group connected to $B_1$ through a single bond such that $B_1$ and $B_2$ form a five-membered ring; $B_2$ is most preferably hydrogen;

(c) X is selected from the group consisting of nil, —$CH_2$—, and —NH—; more preferably, X is nil or —NH—; most preferably, X is —NH—;

(d) Z is an aromatic, substituted or unsubstituted, monocyclic or polycyclic, carbocyclic ring or heterocyclic ring; more preferably, Z is an aromatic, monocyclic, carbocyclic ring; even more preferably, Z is a phenyl or napthalene ring; most preferably, Z is a phenyl ring; preferably $L_4$ and X are substituted on Z in an meta or para fashion; most preferably $L_4$ and X are substituted on Z in apara fashion;

(e) $L_1$, $L_2$, and $L_3$ are each, independently, selected from the group consisting of nil, —NH—, —O—, —S—, —C(O)—, —$CF_2$—, alkyl, alkenyl, cycloalkyl, aryl, arylalkyl, arylalkenyl, —C(O)NH—, —NH—$SO_2$—$R^1$—, —C(O)—$R^2$—, —C(O)—$R^3$—O—, —C(O)—$R^4$—S—, —C(O)—$R^5$—NH—, —NH—$R^6$—, —O—$R^7$—, —C(O)O—$R^8$—, —C(O)NH—$R^9$—, —NHC(O)—$R^{10}$, —OC(O)$R^{11}$, and —C(O)—CH($R^{12}$)—N($R^{13}$)—Y—, wherein $R^1$, $R^2$, $R^3$, $R^4$, $R^5$, $R^6$, $R^7$, $R^8$, $R^9$, $R^{10}$, and $R^{11}$ are, independently, selected from the group consisting of alkyl, alkenyl, cycloalkyl, aryl, arylalkyl, arylalkenyl, alkylamino, protected alkylamino, arylamino, protected arylamino, arylalkylamino, protected arylalkylamino, wherein $R^{12}$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{13}$ is hydrogen, or $R^{12}$ and $R^{13}$ together form a monocyclic or polycyclic heterocyclic ring including the nitrogen to which $R^{13}$ is bonded, and wherein Y is nil or —C(O)—CH($R^{14}$)—N($R^{15}$)— wherein $R^{14}$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{15}$ is hydrogen, or $R^{14}$ and $R^{15}$ together form a second monocyclic or polycyclic heterocyclic ring including the nitrogen to which $R^{15}$ is bonded; more preferably, $L_1$, $L_2$, and $L_3$ are, independently, selected from the group consisting of, —NH—, —O—, —S—, —C(O)—, alkyl, aryl (the most preferred aryl being phenyl), —C(O)NH—, —C(O)—$R^2$—, —C(O)—$R^3$—O—, —C(O)—$R^4$—S—, —C(O)—$R^5$—NH—, —NH—$R^6$—, —O—$R^7$—, —C(O)O—$R^8$—, —C(O)NH—$R^9$—, —NHC(O)—$R^{10}$, —OC(O)$R^{11}$, and —C(O)—CH($R^{10}$)—N($R^{11}$)—Y—, wherein $R^1$, $R^2$, $R^3$, $R^4$, $R^5$, $R^6$, $R^7$, $R^8$, and $R^9$ are, independently, more preferably selected from the group consisting of alkyl and aryl, and wherein $R^{12}$ is more preferably selected from the group consisting of hydrogen, alkyl, aryl, arylalkyl, alkylamino, protected alkylamino, arylamino, protected arylamino, arylalkylamino, protected arylalkylamino, and —AA wherein —AA is an amino acid side chain, and $R^{13}$ is hydrogen, or $R^{12}$ and $R^{13}$ together form a monocyclic or polycyclic heterocyclic ring including the nitrogen to which $R^{13}$ is bonded; and wherein Y is more preferably nil; $R^{12}$ is most preferably selected from the group consisting of hydrogen, alkyl, cycloalkyl, aryl, arylalkyl, and —AA; $R^{13}$ is most preferably hydrogen;

(f) $L_4$ is nil or —C(O)—; most preferably, $L_4$ is —C(O)—;

(g) P is a poly(alkylene oxide) polymer selected from the group consisting of a linear poly(alkylene oxide), a branched chain poly(alkylene oxide), and a star poly(alkylene oxide); more preferably, P is a linear poly(alkylene oxide) (wherein the linear poly(alkylene oxide) is more preferably a homopolymer or copolymer of poly(propylene oxide) or a homopolymer or copolymer of poly(ethylene oxide)) or a branched chain poly(alkylene oxide); most preferably, P is a linear poly(alkylene oxide) (wherein the linear poly(alkylene oxide) is more preferably a homopolymer of poly(propylene oxide) or a homopolymer of poly(ethylene oxide) and is most preferably or a homopolymer of poly(ethylene oxide));

(h) n is an integer from 1 to about 100; wherein when P is linear poly(alkylene oxide), n is more preferably 1 or 2 and is most preferably 1; wherein when P is a branched chain poly(alkylene oxide), n is more preferably from about 2 to about 30, even more preferably from about 2 to about 20, and most preferably from about 2 to about 10; wherein when P is a star poly (alkylene oxide), n is more preferably from about 4 to about 100;

(i) Q is nil or —O—; most preferably Q is —O—; and (j) A is selected from the group consisting of nil, alkyl, alkenyl, cycloalkyl, aryl, arylalkyl, arylalkenyl, Z', wherein Z' is a saturated, unsaturated or aromatic, monocyclic or polycyclic, carbocyclic ring or heterocyclic ring; —C(O)—Z'; and —C(O)—$R^{15}$—$CF_3$, wherein $R^{15}$ is nil or alkyl; and

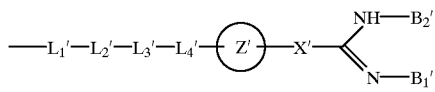

wherein $L_1'$, $L_2'$, $L_3'$, Z', X', $B_1'$, and $B_2'$ are defined as for, respectively, $L_1$, $L_2$, $L_3$, Z, X, $B_1$ and $B_2$; more preferably, A is alkyl (wherein when A is alkyl, A is most preferably a methyl radical) or

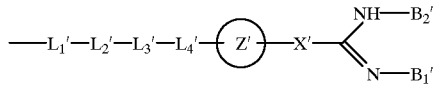

(wherein when A is

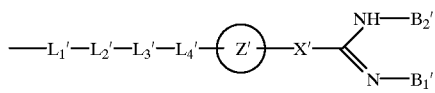

then most preferably, $L_1'=L_1$, $L_2'=L_2$, $L_3'=L_3$, Z'=Z, X'=X, $B_1'=B_1$, and $B_2'=B_2$); wherein the compound is preferably not (I) wherein (I) has the structure:

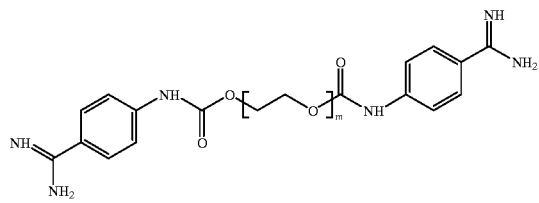

wherein m is an integer from about 3 to about 500.

The ordinarily skilled artisan will appreciate that tautomeric forms will exist in certain compositions of the invention. When tautomer A of the composition is shown, it is understood to include tautomers B and C of that composition although not specifically depicted. To illustrate:

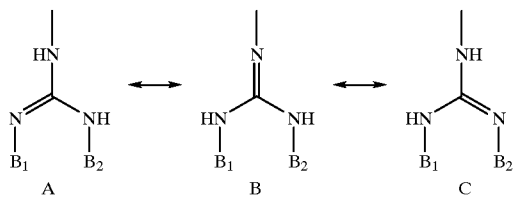

Poly(alkylene oxides)

As used herein, P is a poly(alkylene oxide) polymer selected from the group consisting of a linear poly(alkylene oxide), a branched chain poly(alkylene oxide), and a star poly(alkylene oxide).

Linear Poly(alkylene oxides)

As used herein, a linear poly(alkylene oxide) may be a homopolymer of alkylene oxide monomer units or a copolymer of alkylene oxide monomer units alone or copolymerized with one or more other monomer units wherein the other monomer units bear a structure other than that of an alkylene oxide monomer unit. Wherein the linear poly(alkylene oxide) is a copolymer, the copolymer may contain any pattern of monomer units. For example, the copolymer may contain regular repeats (e.g., A-B-A-B-A-B), irregular repeats (e.g., A-A-B-A-B-B), or may be a block copolymer (e.g., A-A-A-B-B-B).

Wherein P is a linear poly(alkylene oxide) compounds of the present invention have a preferred average molecular weight from about 350 daltons to about 20,000 daltons, a more preferred average molecular weight from about 2,000 daltons to about 15,000 daltons, an even more preferred average molecular weight from about 3,000 daltons to about 10,000 daltons, and a most preferred average molecular weight from about 3,000 daltons to about 5,000 daltons. An exception to this is wherein A is:

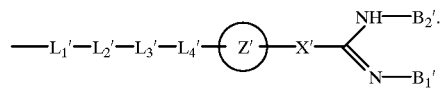

In this exception, wherein P is a linear poly(alkylene oxide), the compound has a preferred average molecular weight from about 400 daltons to about 35,000 daltons, a more preferred average molecular weight from about 1,500 daltons to about 20,000 daltons, an even more preferred average molecular weight from about 3,400 daltons to about 10,000 daltons, and a most preferred average molecular weight from about 3,400 daltons to about 8,000 daltons.

Similarly, linear poly(alkylene oxides) are preferably comprised of from about 5 to about 1000 monomer units, more preferably from about 20 to about 500 monomer units, even more preferably from about 60 to about 250 monomer units, and most preferably from about 60 to about 200 monomer units.

Preferably, the poly(alkylene oxide) is comprised of ethylene oxide and/or propylene oxide monomer units. In a preferred embodiment of the present invention, a linear poly(alkylene oxide) is a homopolymer comprised of ethylene oxide monomer units or propylene oxide monomer units. A linear homopolymer of poly(ethylene oxide) can be represented as follows:

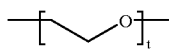

wherein t is the number of repeating ethylene oxide monomer units. A linear homopolymer of poly(propylene oxide) can be represented as follows:

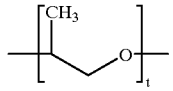

wherein t is the number of repeating propylene oxide monomer units.

As used herein, copolymers of linear poly(alkylene oxides) may be copolymers of alkylene oxide monomer units only or copolymerized with one or more other monomer units wherein the other monomer units bear a structure other than that of an alkylene oxide monomer unit. Wherein the linear poly(alkylene oxide) is a copolymer of alkylene oxide monomer units only, preferably from about 20% to about 99% of the total number of monomer units are ethylene oxide monomer units, and, preferably, from about 1% to about 80% of the total number of monomer units are propylene oxide monomer units.

Wherein the linear poly(alkylene oxide) is a copolymer of alkylene oxide monomer units and one or more other monomer units bearing a structure other than that of a alkylene oxide monomer unit, preferably from about 50% to about 99% of the total number of monomer units are alkylene oxide monomer units, more preferably from about 70% to about 99% of the total number of monomer units are alkylene oxide monomer units, and most preferably from about 80% to about 99% of the total number of monomer units are alkylene oxide monomer units.

An example of a suitable linear poly(alkylene oxide) polymer is a difunctional 2000 molecular weight poly (ethylene glycol) endcapped with propyl amine moieties which is obtainable under the trade name Jeffamine® ED 2003 from Huntsman Chemical Corp., Houston, Tex. The following non-limiting examples further illustrate linear poly(alkylene oxide) copolymers:

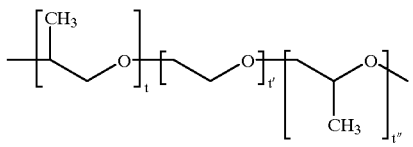

wherein t, t', and t" are each, independently, the number of repeating monomer units;

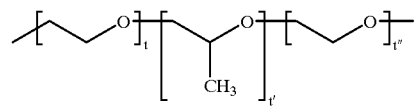

wherein t, t', and t" are each, independently, the number of repeating monomer units.

The following non-limiting examples further illustrate linear copolymers of alkylene oxide monomer units copolymerized with one or more other monomer units wherein the other monomer units bear a structure other than that of an alkylene oxide monomer unit:

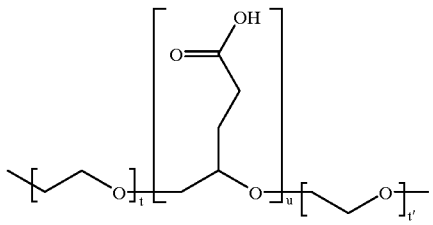

(available from Shearwater Polymers, Inc.) wherein t, u, and t' are each, independently, the number of repeating monomer units;

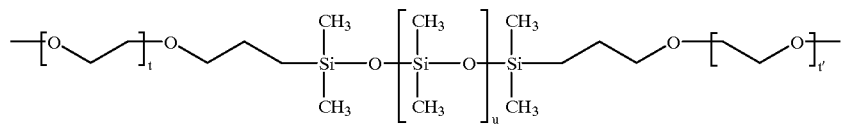

(available from Gelest, Inc.) wherein t, u, and t' are each, independently, the number of repeating monomer units; and

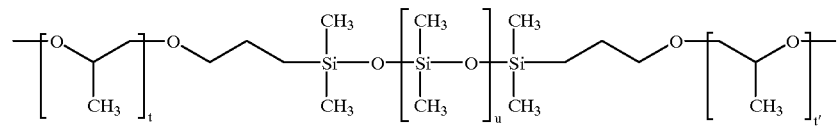

(available from Gelest, Inc.) wherein t, u, and t' are each, independently, the number of repeating monomer units.

Branched Chain Poly(alkylene oxides)

In order to increase the functionality of P, polymers which have multiple "arms" such as branched chain poly(alkylene oxides) are used. A branched chain poly(alkylene oxide) is comprised of one or more linear poly(alkylene oxide) polymers attached to one or more functional monomers. Functional monomers are defined as those monomers bearing reactive functional groups. These reactive functional groups can be utilized for coupling with other functional groups, such as the hydroxyl group of a linear poly(alkylene oxide) polymer. Examples of such functional groups include, but are not limited to, carboxylic acids, alcohols, and amines.

Wherein P is a branched chain poly(alkylene oxide), from about 50% to about 99% of the total number of monomer units are alkylene oxide monomer units, more preferably from about 70% to about 99% of the total number of monomer units are alkylene oxide monomer units, and most preferably from about 80% to about 99% of the total number of monomer units are alkylene oxide monomer units.

Wherein P is a branched chain poly(alkylene oxide) compounds of the present invention have a preferred average molecular weight from about 5,000 daltons to about 100,000 daltons, a more preferred average molecular weight from about 7,000 daltons to about 50,000 daltons, and a most preferred average molecular weight from about 10,000 daltons to about 50,000 daltons.

The following non-limiting examples further illustrate branched chain poly(alkylene oxides):

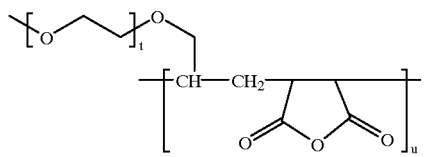

and the derivatives thereof, such as, for example, the hydrolysis product of, wherein t and u are each, independently, the number of repeating monomer units;

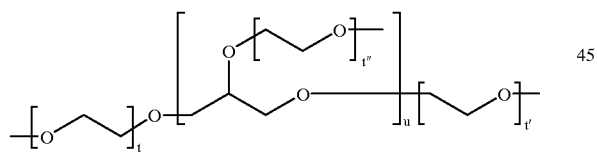

wherein t, t', t", and u are each, independently, the number of repeating monomer units;

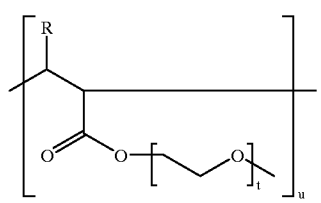

wherein t and u are each, independently, the number of repeating monomer units and R is selected from, for example, hydrogen and alkyl. Such polymers also include analogs thereof, such as, for example, wherein alkoxylation (e.g. ethoxylation), is selected or limited, for example:

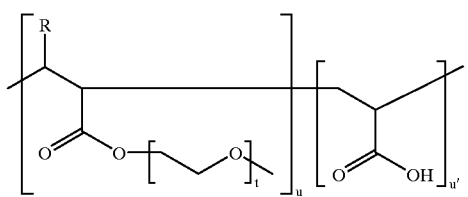

wherein t, u, and u' are each, independently, the number of repeating monomer units and R is selected from, for example, hydrogen and alkyl; similarly,

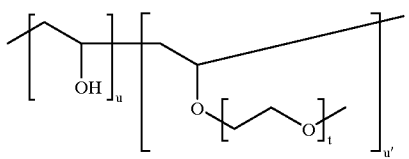

and

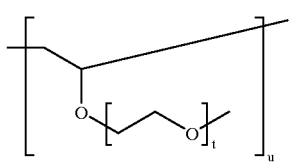

wherein u, u', and t are each, independently, the number of repeating monomer units;

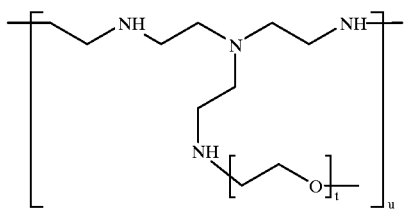

wherein t and u are each, independently, the number of repeating monomer units;

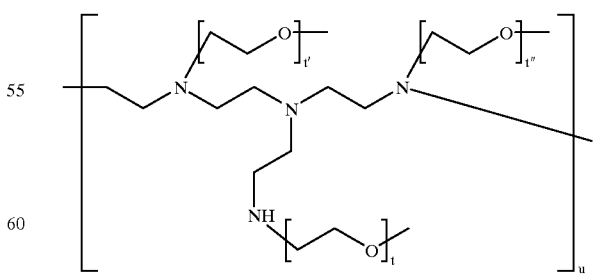

wherein t, t', t" and u are each, independently, the number of repeating monomer units; and

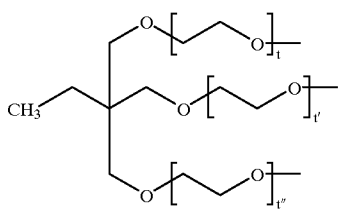

(ethoxylated trimethylolpropane) wherein t, t', t" and u are each, independently, the number of repeating monomer units.

Star Poly(alkylene oxides)

Star poly(alkylene oxides) may also be utilized to further increase the functionality of P. A discussion of the preparation of star poly(ethylene oxides) may be obtained from Gnanou, Y., P. Lutz, and P. Rempp, "Synthesis of Star-Shaped Poly(ethylene oxide)", *Makromolecular Chemistry*, Vol. 189 (1988) pp. 2885–2892. Furthermore, many star poly(alkylene oxides) are commercially available. Such star poly(alkylene oxides) will have a central core which may, but need not be, polymerized to form a polycore. Such cores comprise a predetermined number of active sites to which a linear or branched chain poly(alkylene oxide) is coupled to produce a known number of arms. See also, U.S. Pat. No. 5,648,506, Desai et al., 1997. Examples of cores which may be utilized for star poly(alkylene oxides) include, but are not limited to, divinyl benzene, polymerized divinyl benzene, sugars, including, for example, cyclodextrins, and ethylene diamine. The number of "arms" may vary, but is preferably from about 4 to about 100.

Wherein P is a star poly(alkylene oxide), from about 80% to about 99% of the total number of monomer units are alkylene oxide monomer units, more preferably from about 90% to about 99% of the total number of monomer units are alkylene oxide monomer units, and most preferably from about 95% to about 99% of the total number of monomer units are alkylene oxide monomer units.

Wherein P is a star poly(alkylene oxide) compounds of the present invention have a preferred average molecular weight from about 10,000 daltons to about 500,000 daltons, a more preferred average molecular weight from about 10,000 daltons to about 100,000 daltons, and a most preferred average molecular weight from about 10,000 daltons to about 50,000 daltons.

A four-arm star poly(alkylene oxide) may be exemplified by the illustration below:

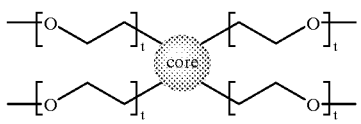

wherein t is the number of repeating monomer units.

More specifically, the following is a non-limiting example of a star poly(alkylene) oxide having an ethylene diamine core:

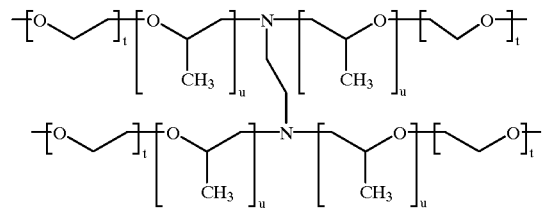

wherein t and u are each, independently, the number of repeating monomer units.

FURTHER EXEMPLIFICATION OF COMPOUNDS OF THE PRESENT INVENTION

The following non-limiting examples serve to further illustrate various compounds of the present invention:

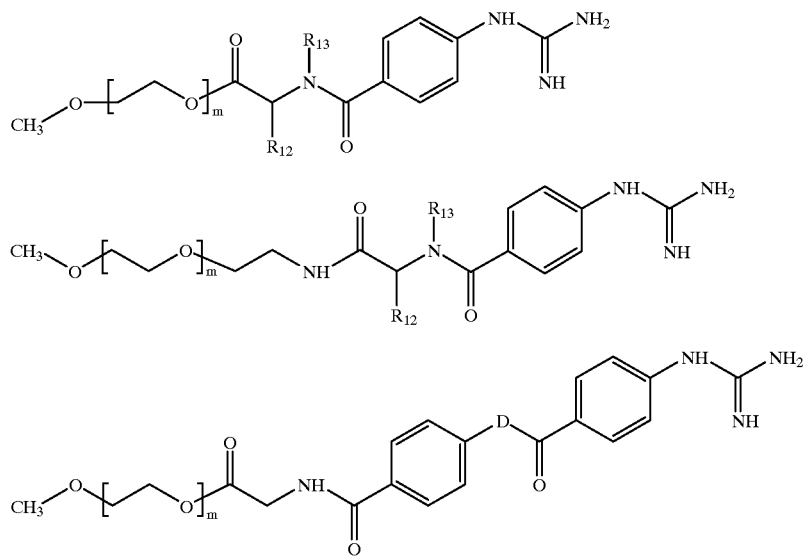

-continued

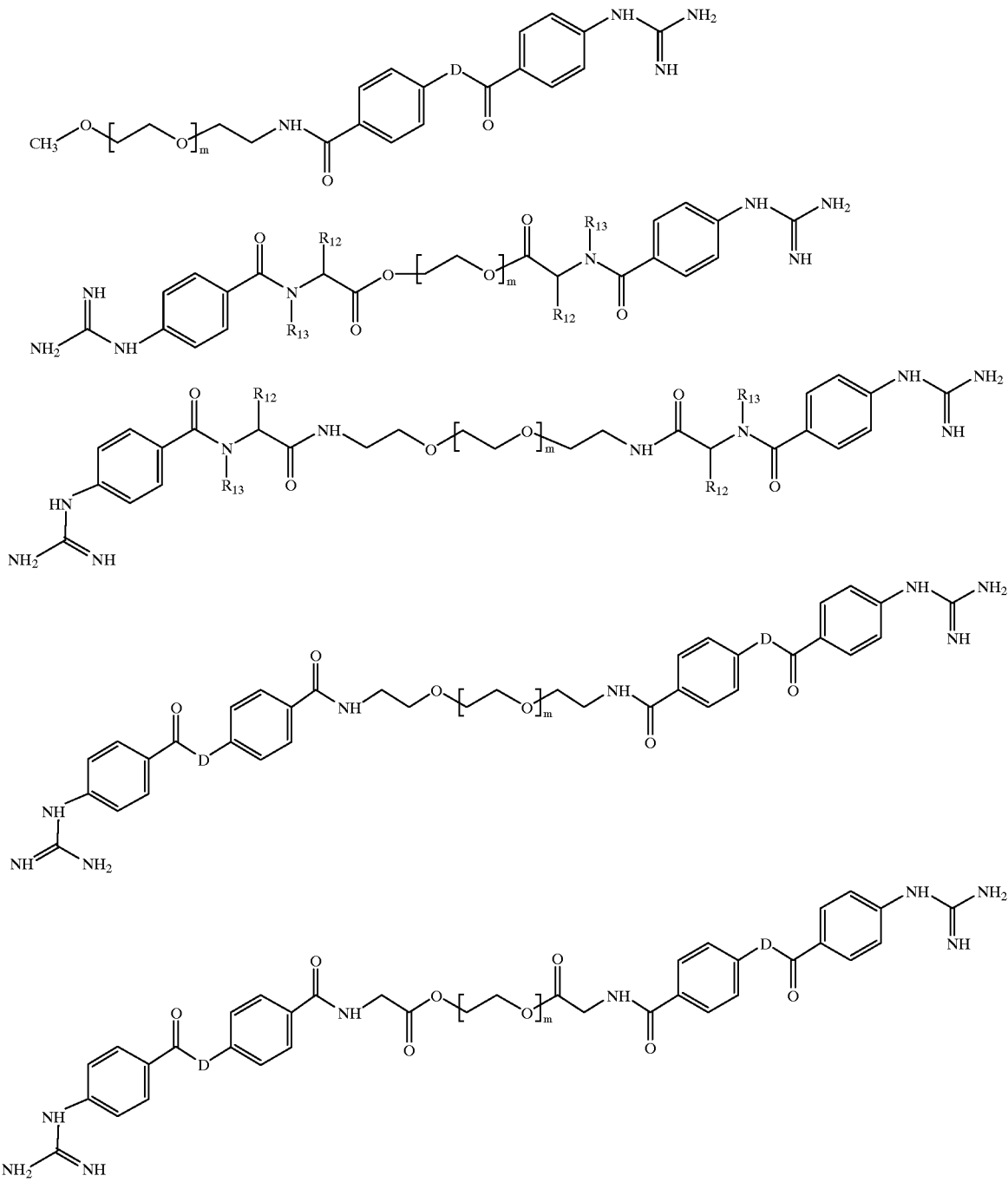

wherein $R^{12}$ is selected from the group consisting of hydrogen, alkyl, cycloalkyl, aryl, arylalkyl, and —AA; $R^{13}$ is hydrogen; D is selected from the group consisting of —O—, —S—, and —NH—; and wherein m is an integer from about 5 to about 1000 monomer units, more preferably from about 20 to about 500 monomer units, even more preferably from about 60 to about 250 monomer units, and most preferably from about 60 to about 200 monomer units; and

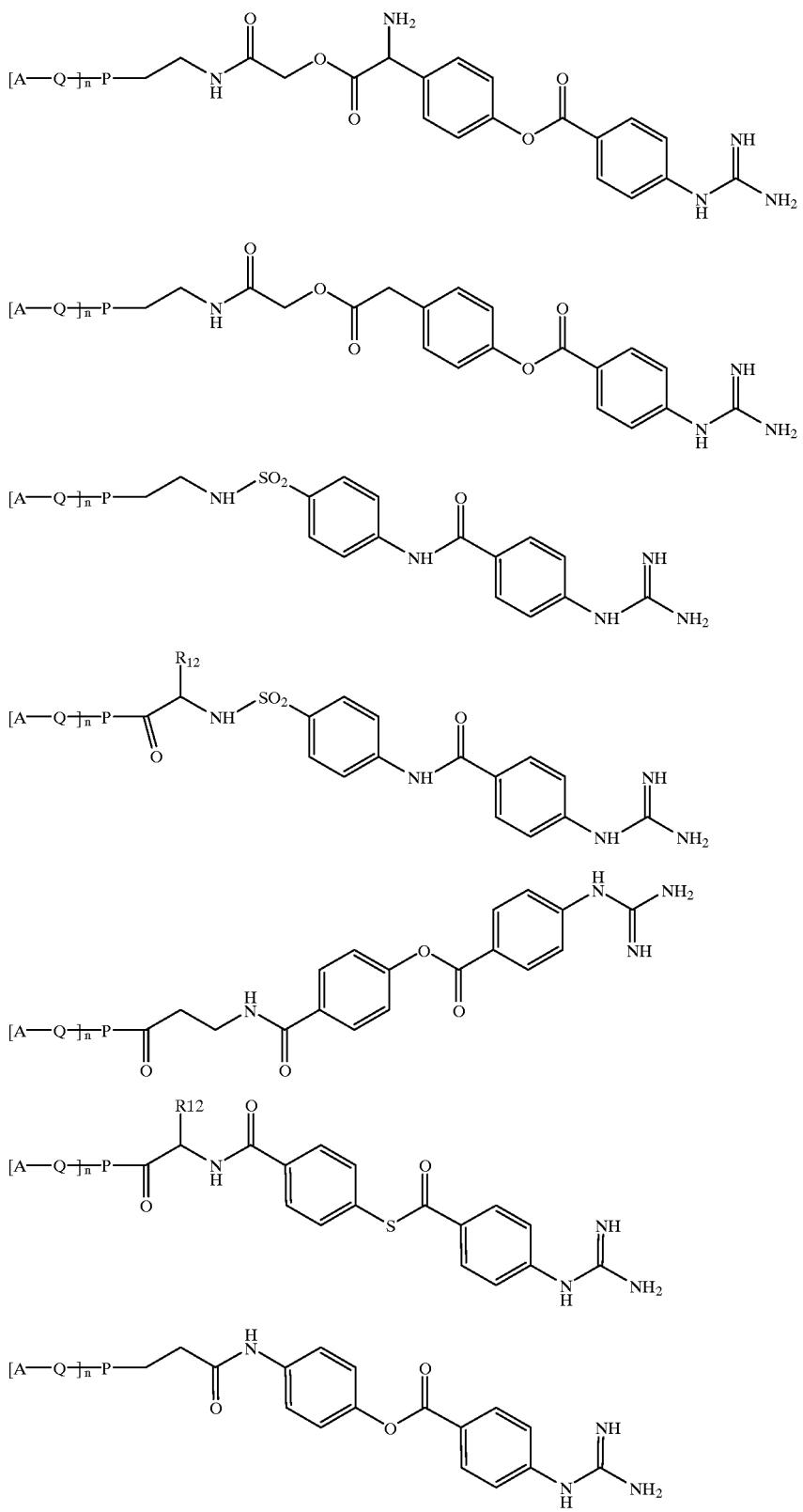

-continued
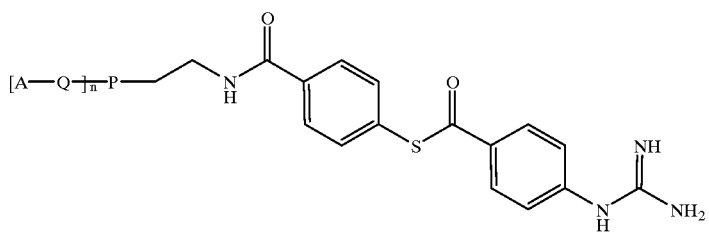
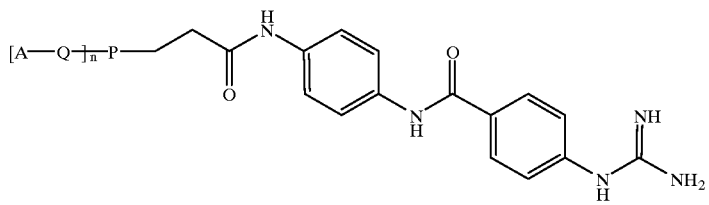
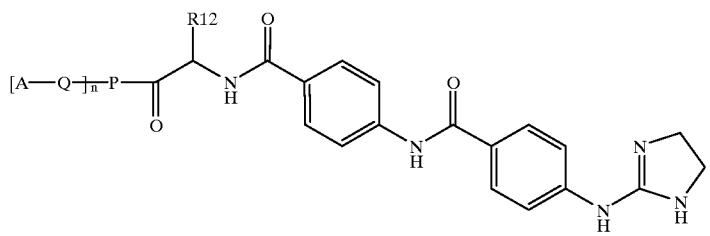
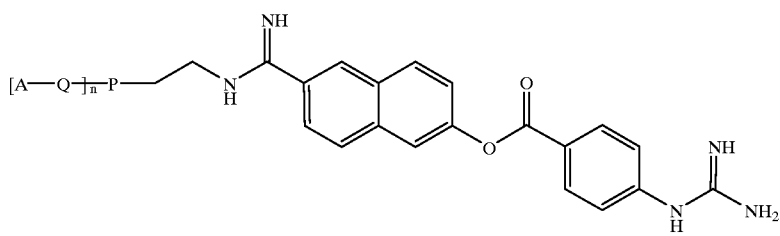
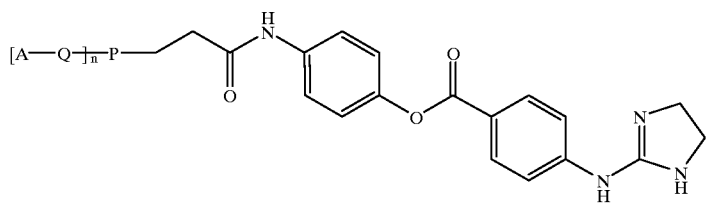
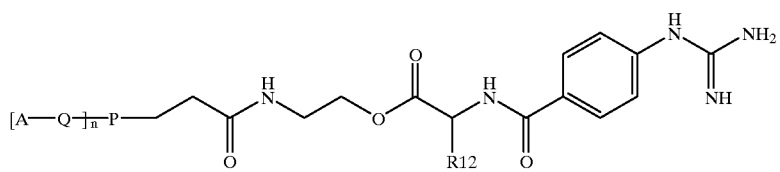
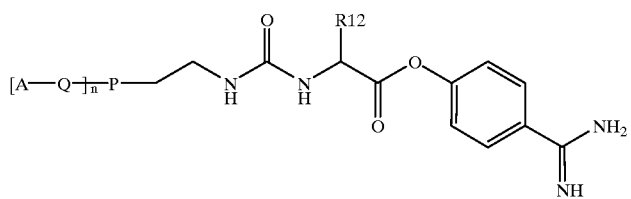
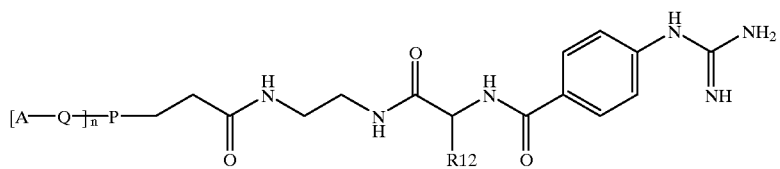

-continued

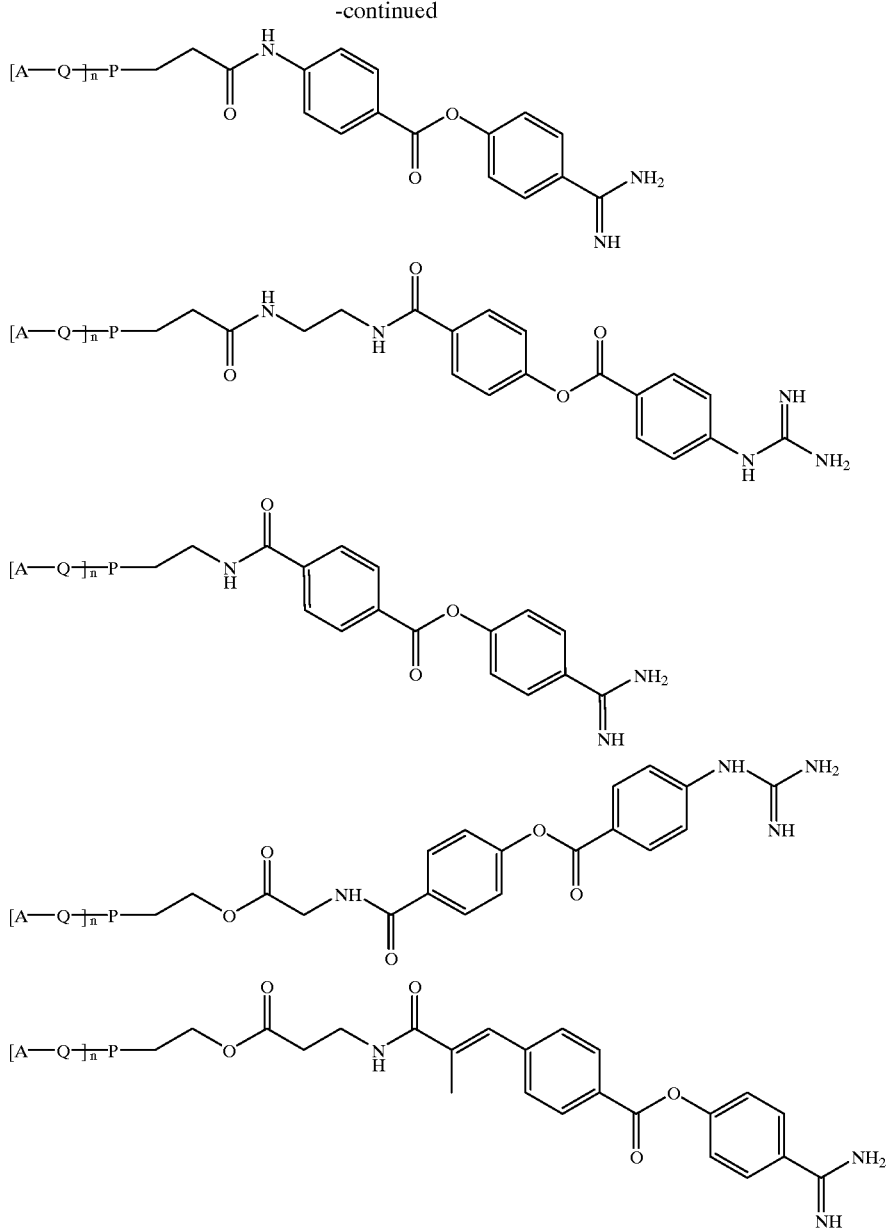

METHODS OF MAKING THE PRESENT COMPOUNDS

The compounds of the present invention are prepared according to methods which are well-known to those skilled in the art. The starting materials used in preparing the compounds of the invention are known, made by known methods, or are commercially available as a starting material.

It is recognized that the skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The skilled artisan will readily appreciate that certain reactions are best carried out when other functionalities are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

The compounds of the present invention may have one or more chiral center. As a result, one may selectively prepare one optical isomer, including diastereomers and enantiomers, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as through the use of, for example, chiral salts and chiral chromatography.

In addition, it is recognized that one optical isomer, including a diastereomer and enantiomer, or a stereoisomer, may have favorable properties over the other. Thus, when disclosing and claiming the invention, when one racemic mixture is disclosed, it is clearly contemplated that both optical isomers, including diastereomers and enantiomers, or stereoisomers substantially free of the other are disclosed and claimed as well.

The following provides general synthetic methods of preparing esters and amides of poly(alkylene oxide) polymers. Further, non-limiting examples illustrate more specifically the methods of making various compounds of the present invention.

As used herein, the following abbreviations are used:

| Reagent | Abbreviation |
| --- | --- |
| N,N-dimethylformamide | DMF |
| N,N-dimethylacetamide | DMA |
| 1-methyl-2-pyrrolidinone | NMP |
| 1,3-dicyclohexylcarbodiimide | DCC |
| 1,3-diisopropylcarbodiimide | DIC |
| 1-(3-dimethylaminopropyl)-3-carbodiimide hydrochloride | EDCI |
| 4-dimethylaminopyridine | DMAP |
| 1-hydroxybenzotriazole hydrate | HOBt |

Esterification of Poly(alkylene oxides):

A poly(alkylene oxide) polymer optionally having, for example, a methyl ether termination at one end of the polymer and containing at least one free hydroxyl is dissolved in solvent(s) suitable for esterification. Preferred solvents for esterification include, but are not limited to, acetonitrile, DMF, DMA, p-dioxane, NMP, dichloromethane, and chloroform. More preferred solvents include acetonitrile, DMF, p-dioxane, NMP, and dichloromethane. The most preferred solvents are dichloromethane, DMF, and NMP.

Under an inert atmosphere, the polymer and a suitably protected carboxylic acid are thoroughly dissolved in an appropriate solvent at ambient temperature. A coupling agent is then added. Coupling agents include, but are not limited to DCC, DIC, EDCI. Esterification of the poly (alkylene oxide) may be accomplished more readily with the addition of, for example, 0.1–10.0 equivalents of DMAP.

The reaction is typically stirred at ambient temperature for about 8 to 18 hours. The reaction may be monitored for completion using silica TLC and Dragendorff's reagent (6.6 g barium chloride, 0.11 g bismuth subnitrate, 2.7 g potassium iodide in water (73 mL) and acetic acid (15 mL)); poly(alkylene oxide) derivatives are visualized by a characteristic orange stain). Upon completion of the reaction, the reaction solution is filtered and the filtrate is diluted with diethyl ether at a temperature preferably between about –10° C. and about 25° C. and most preferably between 0° C. and +4° C., until a precipitate is observed. Alternatively, the filtrate is poured into an excess of rapidly stirred diethyl ether at a temperature preferably between about –10° C. and about 25° C. and most preferably between 0° C. and +4° C., to precipitate the esterified polymer. The solid is collected, washed with ether, dried and weighed. Further purification, when necessary, is accomplished via recrystallization from, for example, warm ethanol.

Amides may be prepared utilizing conditions similar to those given above, using the appropriate starting materials and reagents, as will be readily apparent to one skilled in the art.

The following non-limiting examples further illustrate the compositions of the present invention, including those embodiments which are neither esters nor amides of the poly(alkylene oxides):

EXAMPLE 1

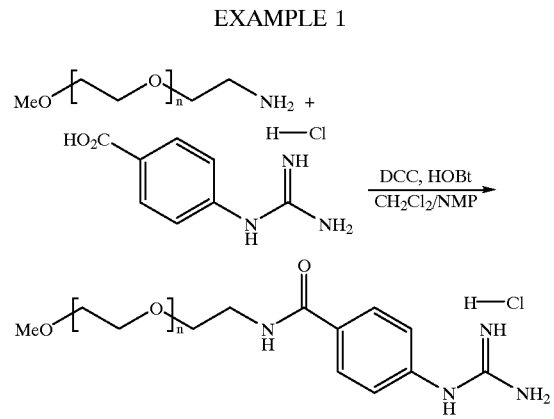

N-4-guanidinobenzoyl-2-aminoethyl-poly(ethylene glycol) monomethyl ether, hydrochloride salt:

2-aminoethyl-poly(ethylene glycol) monomethyl ether ($M_n$~5000, 0.50 g, 0.1 mmol), 4-guanidinobenzoic acid, hydrochloride salt (0.22 g, 1 mmol), and HOBt (0.14 g, 1 mmol) are dissolved in a mixture of NMP and dichloromethane (1:1, v:v) (3 mL). 1,3-dicyclohexylcarbodiimide (DCC) (0.21 g, 1 mmol) is added and the reaction is stirred overnight at ambient temperature. The mixture is filtered, and the filtrate is poured into cold ether. The precipitate is collected, washed with diethyl ether, and recrystallized from warm ethanol to afford N-4-guanidinobenzoyl-2-aminoethyl-poly(ethylene glycol) monomethyl ether, hydrochloride salt as a white powder.

EXAMPLE 2

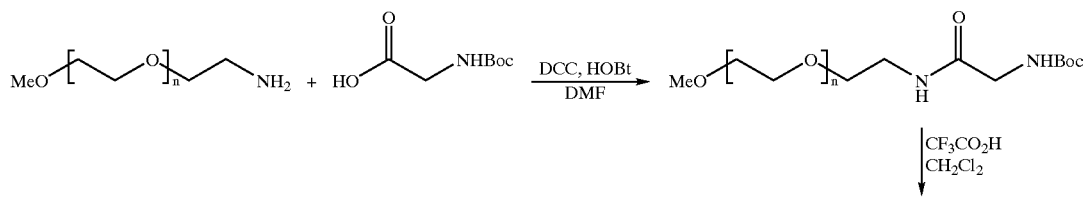

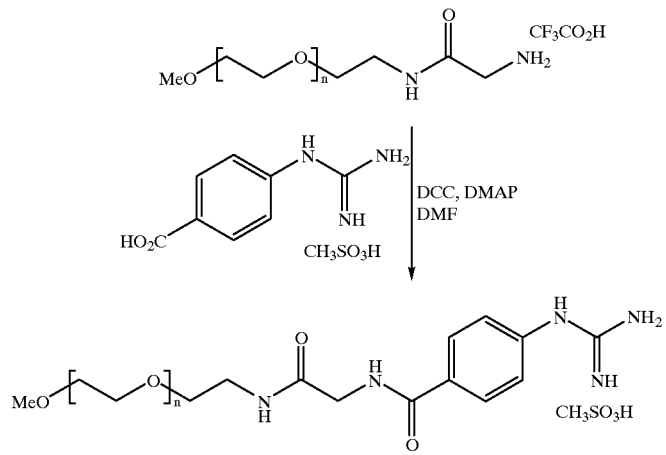

N-[N-(4-guanidinobenzoyl)-glycyl]-2-aminoethyl-poly (ethylene glycol) monomethyl ether, methanesulfonate salt A. N-[N-(tert-butoxycarbonyl)-glycyl]-2-aminoethyl-poly(ethylene glycol) monomethyl ether: 2-aminoethyl-poly(ethylene glycol) monomethyl ether ($M_n$~5000, 1.0 g, 0.2 mmol), N-(tert-butoxycarbonyl)-glycine (0.2 g, 5 eq.), and HOBt (0.14 g, 5 eq.) are dissolved in 20 mL of DMF at ambient temperature under argon. After 10 minutes, DCC (0.2 g, 5 eq.) is added and the reaction is stirred for 18 hours. The reaction is filtered and the filtrate is diluted in cold ether to form a white precipitate. A white solid is collected and recrystallized from warm ethanol giving N-[N-(tert-butoxycarbonyl)-glycyl]-2-aminoethyl-poly(ethylene glycol) monomethyl ether.

B. N-glycyl-2-aminoethyl-poly(ethylene glycol) monomethyl ether, trifluoroacetate salt: The product from step A (0.93 g, 0.2 mmol) is dissolved in 12 mL of a 50% mixture of trifluoroacetic acid in dichloromethane and is stirred at ambient temperature for 4 hours. The reaction mixture is diluted in cold ether to give N-glycyl-2-aminoethyl-poly(ethylene glycol) monomethyl ether, trifluoroacetate salt as a white precipitate which is recovered by filtration.

C. N-[N-(4-guanidinoberzoyl)-glycyl]-2-aminoethyl-poly(ethylene glycol) monomethyl ether, methanesulfonate salt: The product from step B. (0.9 g, 0.19 mmol), 4-guanidinobenzoic acid methanesulfonate salt (0.5 g, 10 eq.), triethylamine (1 eq.), and DMAP (0.2 g, 10 eq.) are dissolved in 25 mL of DMF. DCC (0.4 g, 10 eq.) is added and the solution is stirred at ambient temperature under argon for 18 hours. The solution is filtered of solid and the filtrate is diluted with cold ether until a precipitate is observed. The recovered solid is recrystallized from warm ethanol giving N-[N-(4-guanidinobenzoyl)-glycyl]-2-aminoethyl-poly(ethylene glycol) monomethyl ether, methanesulfonate salt as a white solid.

The following compounds may be prepared according to the method set forth in Example 2, using the appropriate starting materials:

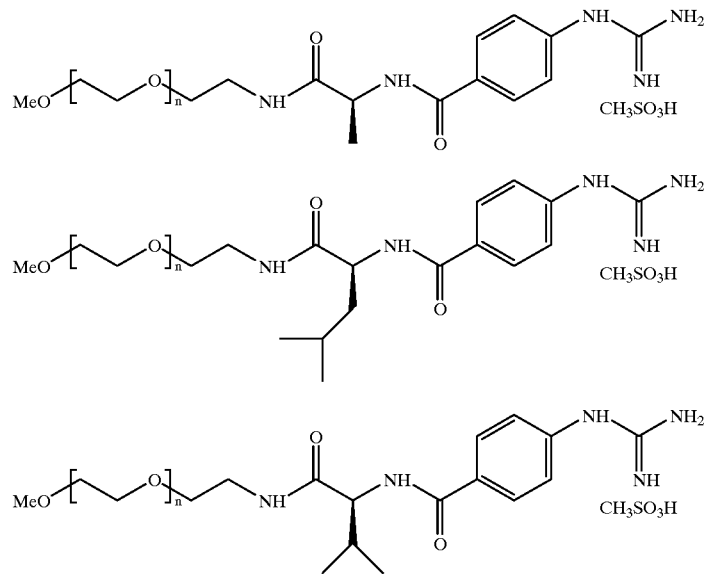

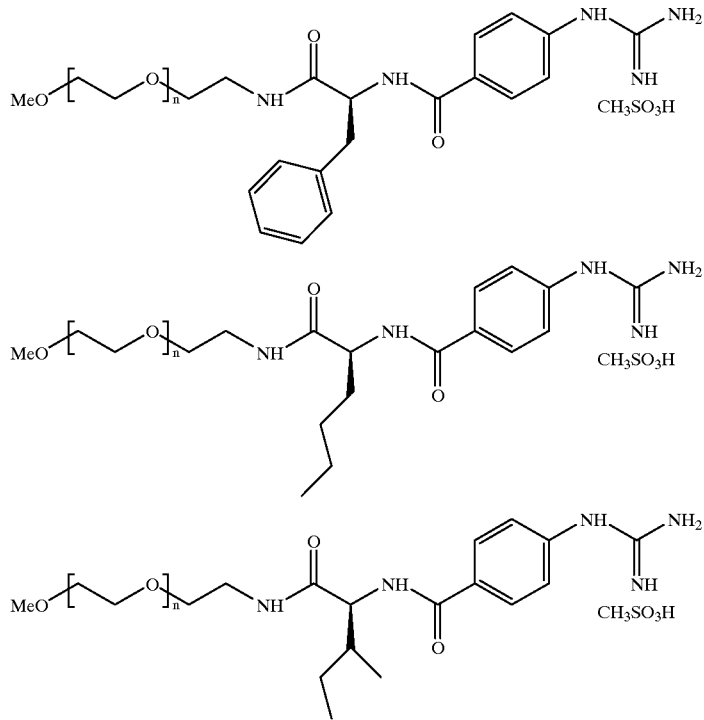
EXAMPLE 3
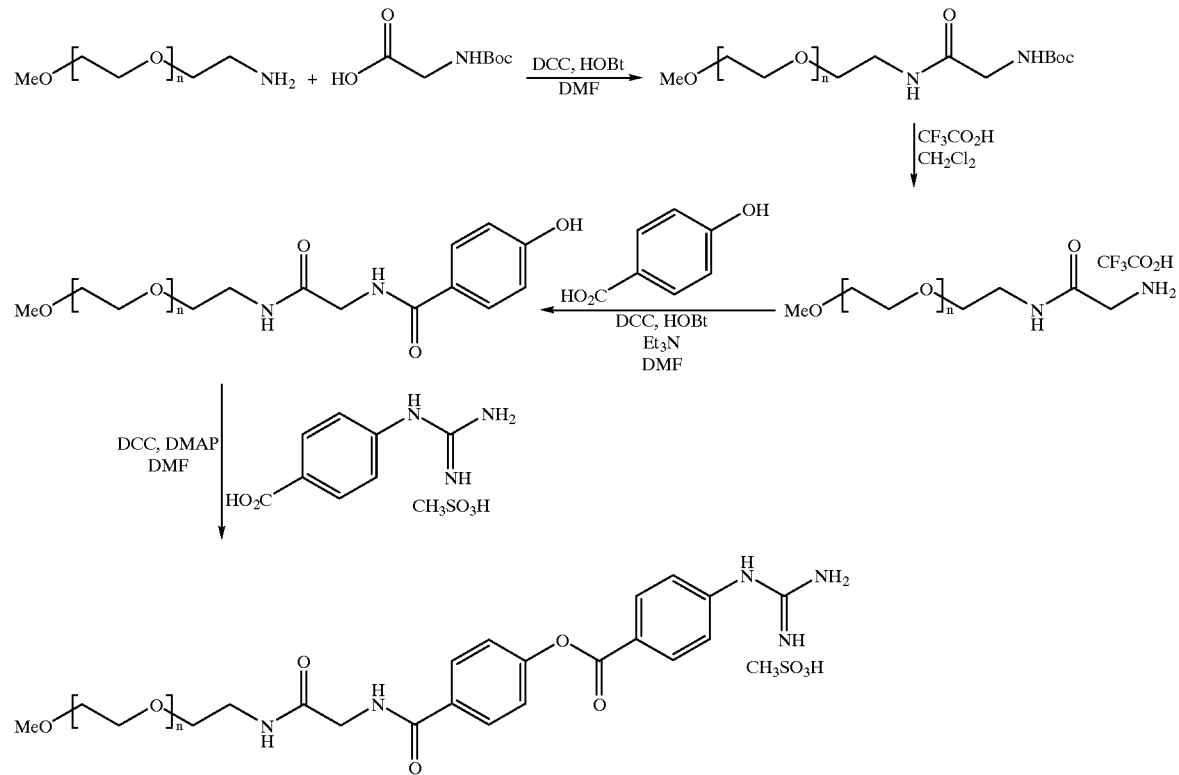

N-[N-4-(4-guanidinobenzoyloxy)-benzoylglycinyl]-2-aminoethyl-poly(ethylene glycol) monomethyl ether, methanesulfonate salt A. N-[N-(tert-butoxycarbonyl)-glycyl]-2-aminoethyl-poly(ethylene glycol) monomethyl ether: 2-aminoethyl-poly(ethylene glycol) monomethyl ether ($M_n$~5000, 1.0 g, 0.2 mmol), N-(tert-butoxycarbonyl)-glycine (0.2 g, 5 eq.), and HOBt (0.14 g, 5 eq.) are dissolved in 20 mL of DMF and stirred at ambient temperature under argon. After 10 minutes, DCC (0.2 g, 5 eq.) is added. The reaction is stirred for 18 hours. The reaction is filtered and the filtrate is diluted in cold ether to form a white precipitate. A white solid is collected and recrystallized from warm ethanol giving N-[N-(tert-butoxycarbonyl)-glycyl]-2-aminoethyl-poly(ethylene glycol) monomethyl ether.

B. N-glycyl-2-aminoethyl-poly(ethylene glycol) monomethyl ether, trifluoroacetate salt: The product from step A (0.93 g, 0.2 mmol) is dissolved in 12 mL of a 50% mixture of trifluoroacetic acid in dichloromethane and is stirred at ambient temperature for 4 hours. The reaction mixture is diluted in cold ether to give N-glycyl-2-aminoethyl-poly(ethylene glycol) monomethyl ether, trifluoroacetate salt as a white precipitate which is recovered by filtration.

C. N-[N-(4-hydroxybenzoyl)-glycinyl]-2-aminoethyl-poly(ethylene glycol) monomethyl ether: The product from step B (0.2 g, 0.04 mmol) is dissolved in 10 mL DMF and stirred at ambient temperature under argon. One equivalent of triethylamine is added. HOBt (10 eq.) and 4-hydroxybenzoic acid (10 eq.) are added. After 10 minutes DCC (0.83 g, 10 eq.) is added and the reaction is stirred overnight. The solution is filtered and the filtrate is diluted with cold ether until a precipitate is observed. The recovered solid is recrystallized from warm ethanol giving N-[N-(4-hydroxybenzoyl)-glycinyl]-2-aminoethyl-poly(ethylene glycol) monomethyl ether as a white solid.

D. N-[N-4-(4-guanidinobenzoyloxy)-benzoylglycinyl]-2-aminoethyl-poly(ethylene glycol) monomethyl ether, methanesulfonate salt: The product from step C, (0.15 g, 0.03 mmol), 4 guanidinobenzoic acid methanesulfonate salt (0.083 g 0.3 mmol), and DMAP (0.05 g, 0.4 mmol) are dissolved in 10 mL of DMF. DCC (0.062 g, 0.3 mmol) is added and the solution is stirred at ambient temperature under argon for 18 hours. The solution is filtered and the filtrate is diluted with cold ether until a precipitate is observed. The recovered solid is recrystallized from warm ethanol giving N-[N-4-(4-guanidinobenzoyloxy)-benzoylglycinyl]-2-aminoethyl-poly(ethylene glycol) monomethyl ether, methanesulfonate salt as a white solid.

EXAMPLE 4

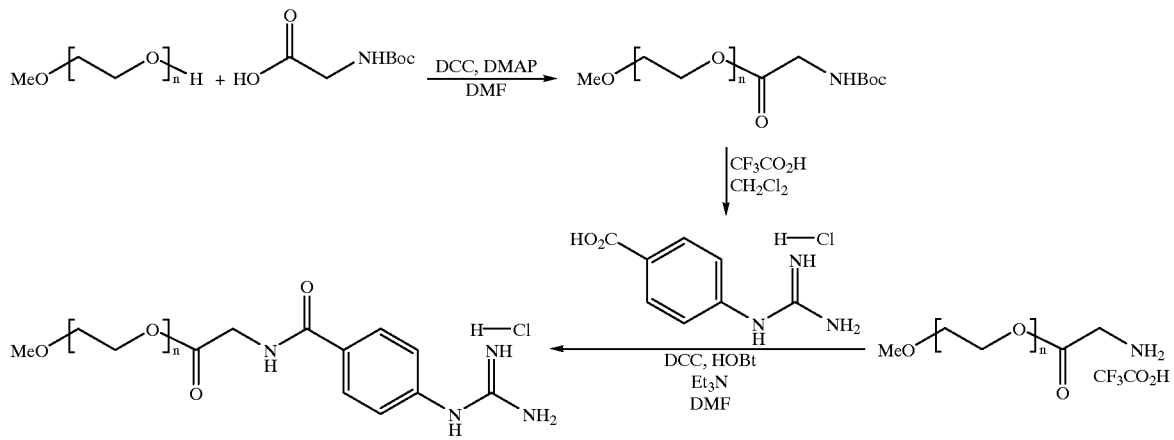

N-(4-guanidinobenzoyl)-glcyl-poly(ethylene glycol) monomethyl ether, hydrochloride salt A. N-(tert-butoxycarbonyl)-glycyl-poly(ethylene glycol) monomethyl ether: Poly(ethylene glycol) monomethyl ether ($M_n$~5,000, 5 g, 1.0 mmol), N-(tert-butoxycarbonyl)-glycine (1.75 g, 10 mmol), and DMAP (0.12 g, 1 mmol) are dissolved in 40 mL of DMF. To this solution is added DCC (2.06 g, 10 mmol) and the mixture stirs at ambient temperature for 18 hours. The reaction is filtered and the filtrate is diluted with cold ether. The resulting white solid is obtained by filtration and washed with ether (3x) to yield N-(tert-butoxycarbonyl)-glycyl-poly(ethylene glycol) monomethyl ether. The solid is recrystallized from warm ethanol.

B. Glycyl-poly(ethylene glycol) monomethyl ether, trifluoroacetate salt: The product from step A (1.03 g, 0.21 mmol) is dissolved in 20 mL of a 50% mixture trifluoroacetic acid in dichloromethane and stirred at ambient temperature for 4 hours. The reaction mixture is diluted in cold ether forming glycyl-poly(ethylene glycol) monomethyl ether as a white precipitate which is recovered by filtration.

C. To the product of step B (0.2 g, 0.04 mmol) is added 4-guanidinobenzoic acid hydrochloride salt (0.086 g, 0.4 mmol), HOBt (0.054 g, 0.4 mmol), and 10 mL DMF. Triethylamine (6 μL) is added, followed by DCC (0.083 g, 0.4 mmol) in one portion and the mixture is stirred overnight at ambient temperature. The reaction is filtered of solids and the filtrate is diluted with ether to form a precipitate which is collected and washed with ether to give a white powder. Recrystallization from warm ethanol affords N-(4-guanidinobenzoyl)-glycyl-poly(ethylene glycol) monomethyl ether, hydrochloride salt as a white solid.

EXAMPLE 5

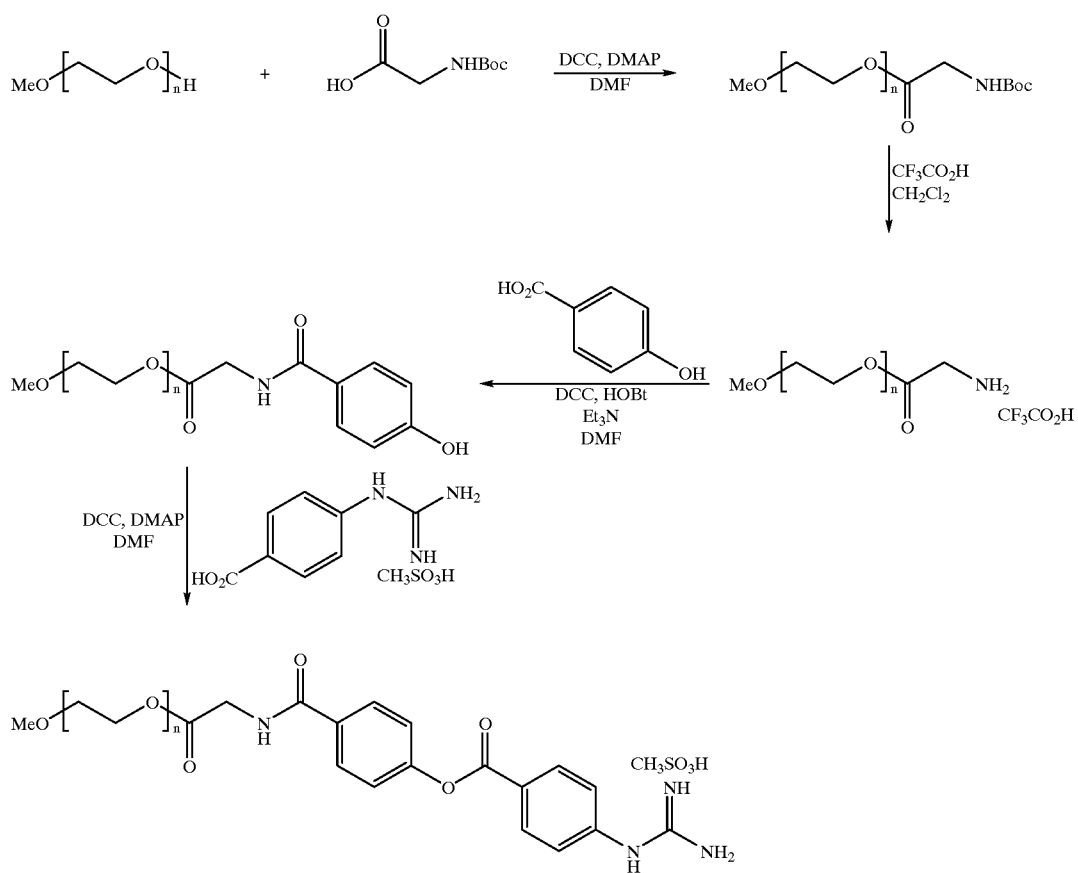

N-[4-(4-guanidinobenzyloxy)-benzoyl]-glycyl-poly(ethylene glycol) monomethyl ether, methanesulfonate salt A. N-(4-hydroxybenzoyl)-glycyl-poly(ethylene glycol) monomethyl ether: Glycyl-poly(ethylene glycol) monomethyl ether, trifluoroacetate salt (prepared according to example 4A–4B; 0.2 g, 0.038 mmol) is dissolved in 10 mL of DMF and stirred at ambient temperature under argon. Triethylamine (1 eq.) is added. HOBt, (0.06 g, 0.44 mmol) and 4-hydroxybenzoic acid (0.06 g, 0.43 mmol) are added to the reaction. DCC (0.09 g, 10 eq.) is added and the reaction is stirred for 16 hours. The product is recovered as N-(4-hydroxybenzoyl)-glycyl-poly(ethylene glycol) monomethyl ether as white solid.

B. N-[4-(4-guanidinobenzyloxy)-benzoyl]-glycyl-poly(ethylene glycol) monomethyl ether, methanesulfonate salt: The product from step A (0.132 g, 0.03 mmol), 4-guanidinobenzoic acid methanesulfonate salt (0.09 g, 0.33 mmol), and DMAP (0.05 g, 0.4 mmol) are dissolved in 10 mL of DMF. DCC (0.07 g, 0.32 mmol) is added, and the solution is stirred at ambient temperature under argon for 18 hours. The solution is filtered and the filtrate is diluted with cold diethyl ether until a precipitate is observed. The recovered solid is recrystallized from warm ethanol giving N-[4-(4-guanidinobenzyloxy)-benzoyl]-glycyl-poly(ethylene glycol) monomethyl ether, methanesulfonate salt, as a white solid.

EXAMPLE 6

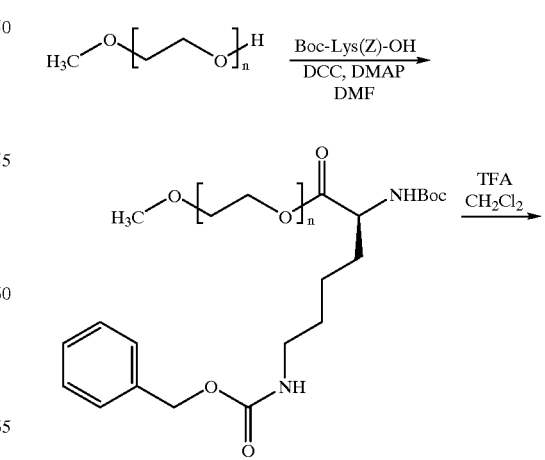

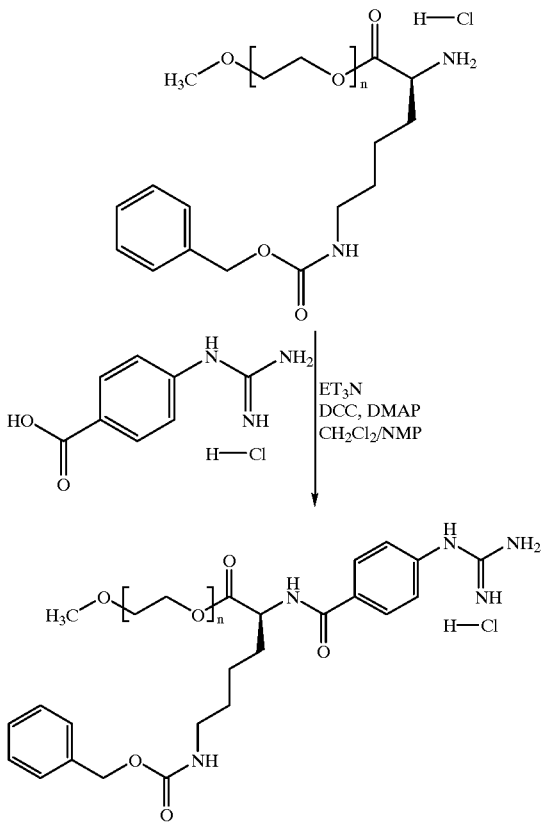

($N^\alpha$-4-guanidinobenzoyl-$N^\epsilon$-benzyloxycarbonyl-L-lysyl)-poly(ethylene glycol) monomethyl ether, hydrochloride salt A. ($N^\alpha$-(tert-butoxycarbonyl)-$N^\epsilon$-benzyloxycarbonyl-L-lysyl)-poly(ethylene glycol) monomethyl ether: Poly(ethylene glycol) monomethyl ether, (Mn=5,000, 2 g, 0.4 mmol) is placed in a reaction vessel. $N^\alpha$-Boc-$N^\epsilon$-benzyloxycarbonyl-L-lysine (1.522 g, 4.0 mmol) and DMAP (0.010 g, 0.08 mmol) are added and the mixture is dissolved in 15 mL DMF. DCC (0.825 g, 4.0 mmol) is added and the resulting solution is stirred under argon for 18 hours. The resulting mixture is filtered and the solids are washed with dichloromethane. The combined filtrates are concentrated in vacuo to approximately 10 mL, then poured into 150 mL of rapidly stirred ether. The resulting precipitate is collected on a glass frit, washed with ether, and dried under suction. The resulting crude powder is recrystallized from warm ethanol and collected on a glass frit, washed with ether and dried under suction to give $N^\alpha$-(tert-butoxycarbonyl)-$N^\epsilon$-benzyloxycarbonyl-L-lysyl-poly(ethylene glycol) monomethyl ether as a white powder.

B. ($N^\epsilon$-benzyloxycarbonyl-L-lysyl)-poly(ethylene glycol) monomethyl ether, trifluoroacetate salt: The product from step A is treated with 10 mL of 50% trifluoroacetic acid in dichloromethane for four hours at ambient temperature. The solution is poured into 150 mL diethyl ether, and the resulting precipitate is collected on a glass frit, washed with ether and dried under suction to produce $N^\epsilon$-benzyloxycarbonyl-L-lysyl-poly(ethylene glycol) monomethyl ether, trifluoroacetate salt as a white solid.

C. ($N^\alpha$-4-guanidinobenzoyl-$N^\epsilon$-benzyloxycarbonyl-L-lysyl)-poly(ethylene glycol) monomethyl ether, hydrochloride salt: The product from step B (0.1 g, 0.02 mmol) is placed in a reaction vessel equipped with a magnetic stirring bar. HOBt (0.03 g, 0.2 mmol) and 4-guanidinobenzoic acid hydrochloride salt (0.04 g, 0.2 mmol) are added, and the mixture is dissolved in 2 mL dichoromethane and 1 mL NMP. Triethylamine (5.6 μL) is added, followed by DCC (0.04 g, 0.2 mmol) and the resulting solution is stirred under argon for 16 hours at ambient temperature. The resulting mixture is filtered and the solids are washed with dichloromethane. The filtrates are combined and poured into ether. The resulting precipitate is collected on a glass frit and washed with diethyl ether. The white powder obtained is recrystallized from warm ethanol to afford ($N^\alpha$-4-guanidinobenzoyl-$N^\epsilon$-benzyloxycarbonyl-L-lysyl)-poly(ethylene glycol) monomethyl ether, hydrochloride salt as a white solid.

EXAMPLE 7

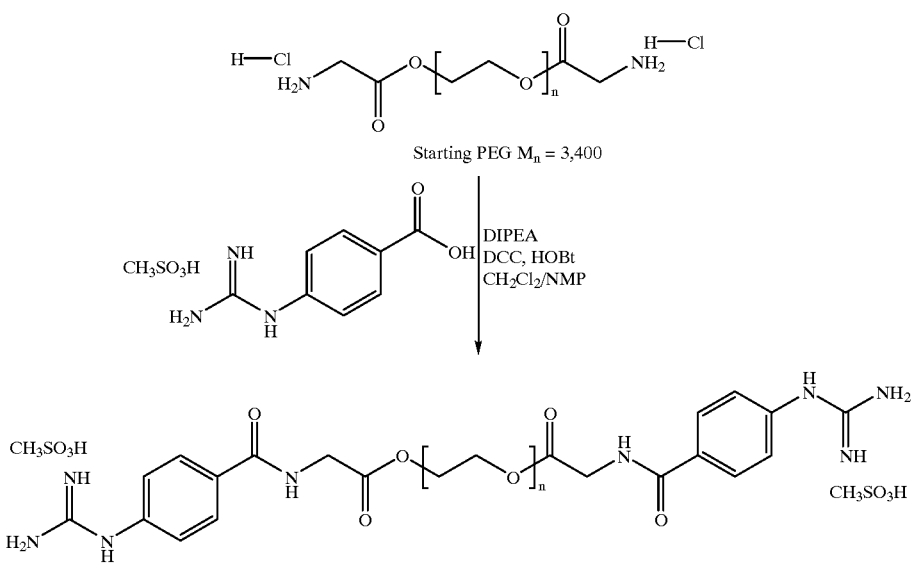

Bis-[N-(4-guanidinobenzoyl)-glycyl]-poly(ethylene glycol) methanesulfonate salt

Bis-glycyl-poly(ethylene glycol), hydrochloride salt ($M_n$~3400, 0.4 g, 0.12 mmol), HOBt (0.318 g, 2.35 mmol) and 4-guanidinobenzoic acid methane sulfonate salt (0.65 g, 2.35 mmol) are placed in a reaction vessel, and the mixture is dissolved in dichloromethane (8 mL). Diisopropylethylamine (45 μL) is added, followed by 4 mL NMP. DCC (0.49 g, 2.35 mmol) is added in 2 mL dichloromethane and the resulting solution is stirred under argon for 40 hours at ambient temperature. The mixture is filtered and the filtrate is diluted with diethyl ether to produce a precipitate which is collected on a glass frit. The resulting white powder is dissolved in warm ethanol, filtered, and placed in a refrigerator (4° C.). The resulting crystals are collected on a glass frit, washed with cold ethanol followed by diethyl ether, and dried under suction to give bis-[N-(4-guanidinobenzoyl)-glycyl]-poly(ethylene glycol) methanesulfonate salt as a white powder.

EXAMPLE 8 collected on a glass frit, washed with 200 mL diethyl ether, and dried under suction to give bis-(N-(tert-butoxycarbonyl)-glycyl)-poly(ethylene glycol) as a solid.

B. Bis-glycyl-poly(ethylene glycol), trifluoroacetate salt: The solid from step A is placed in a reaction vessel and treated with 50 mL of trifluoroacetic acid (50% in dichloromethane) and is stirred for one hour. The solution is poured into 800 mL diethyl ether, and the resulting precipitate is collected on a glass frit, washed with 200 mL diethyl ether, and dried under suction.

C. Bis-[N-(4-guanidinobenzoyl)-glycyl]-poly(ethylene glycol), methanesulfonate salt: The product of step B (9.6 g, 1.2 mol), HOBt (1.620 g, 12 mmol) and 4-guanidinobenzoic acid methane sulfonate salt (3.30 g, 12 mmol) are placed in a reaction vessel, and the mixture is dissolved in 100 mL DMF with stirring. Triethylamine (350 μL) is added, followed by DCC (2.48 g, 12 mmol) and the resulting solution is stirred under argon for 16 hours. The mixture is filtered

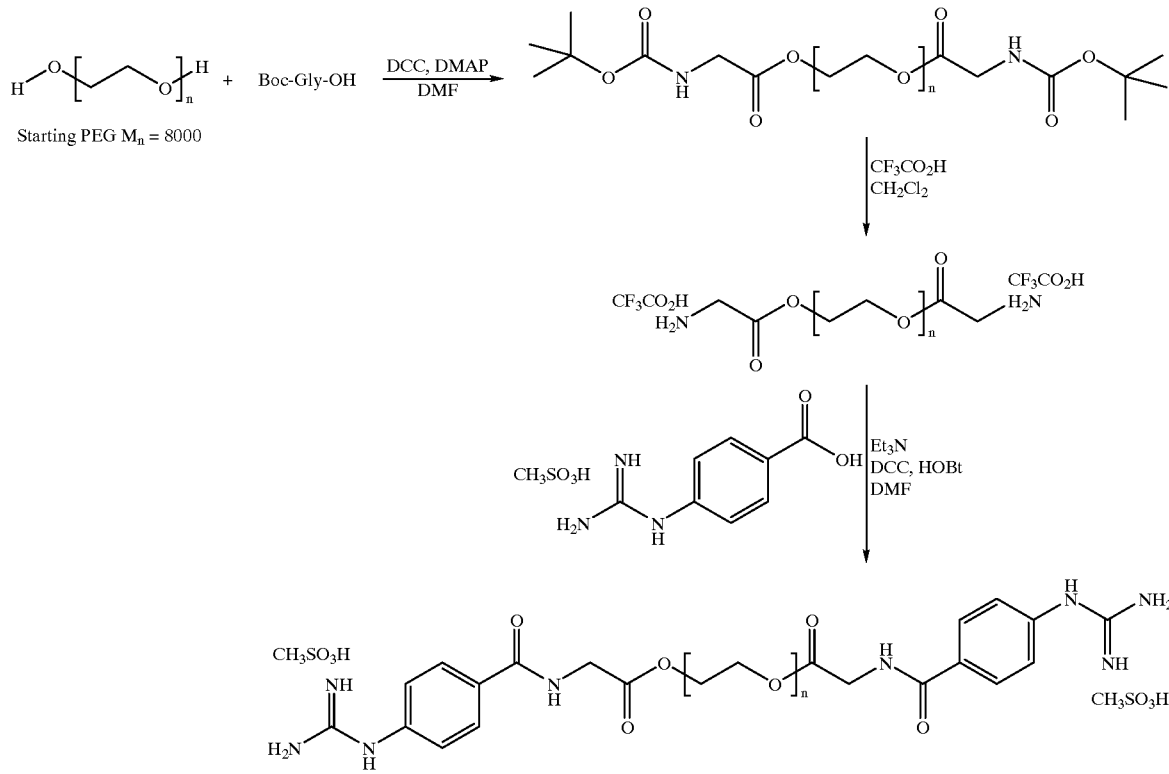

Bis-[N-(4-guanidinobenzoyl)-glycyl]-poly(ethylene glycol), methanesulfonate salt A. Bis-(N-(tert-butoxycarbonyl)-glycyl)-poly(ethylene glycol): Poly(ethylene glycol), ($M_n$~8000, 10 g, 1.25 mmol), N-(tert-butoxycarbonyl)-glycine (2.19 g, 12.5 mmol) and DMAP (0.092 g, 0.75 mmol) are placed in a reaction vessel and the mixture is dissolved in 100 mL of dry DMF with stirring. DCC (2.58 g, 12.5 mmol) is added and the resulting solution is stirred under argon for 18 hours at ambient temperature. The resulting mixture is filtered and the filtrate is poured into 900 mL of ether. The resulting precipitate is and the filtrate is poured into 800 mL of ether. The resulting precipitate is collected on a glass frit, washed with 200 mL ether, and dried under suction. The resulting white powder is dissolved in warm ethanol (400 mL), filtered, and placed in a refrigerator (4° C.) for 72 hours. The resulting crystals are collected on a glass frit and washed with cold ethanol (200 mL) followed by ether (3×200 mL) and dried under suction to give bis-[N-(4-guanidinobenzoyl)-glycyl]-poly (ethylene glycol), methanesulfonate salt as a white powder.

EXAMPLE 9

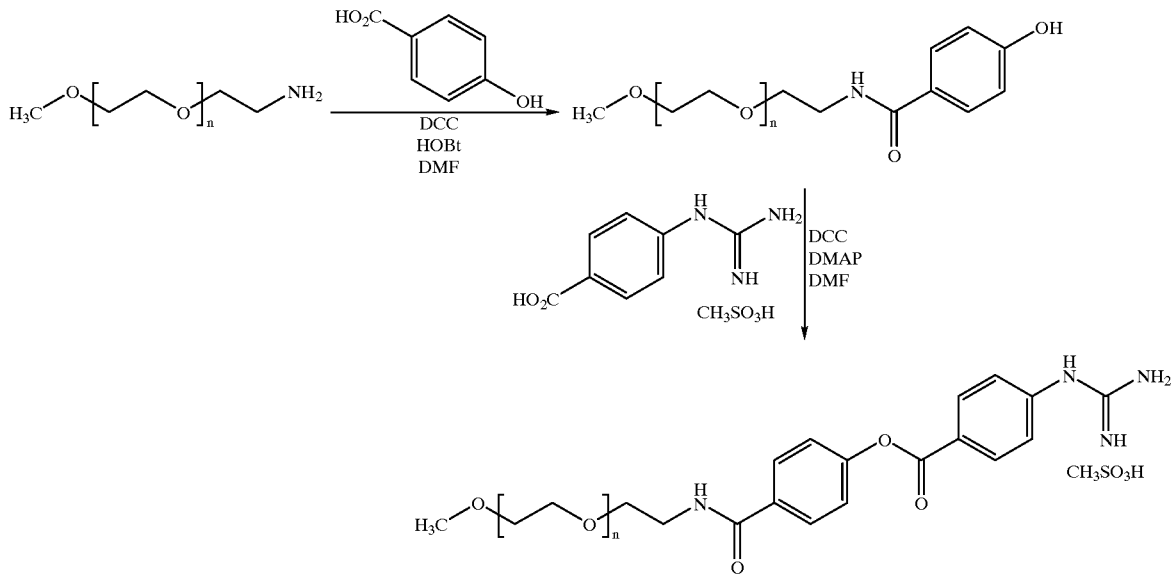

N-[4-(4-guanidinobenzoyloxy)benzoyl]-2-aminoethyl-poly(ethylene glycol) monomethyl ether A. N-(4-hydroxybenzoyl)-2-aminoethyl-poly(ethylene glycol) monomethyl ether: 2-aminoethyl-poly(ethylene glycol) monomethyl ether, $M_n$~5,000 (1 g, 0.2 mmol), 4-hydroxybenzoic acid (0.14 g, 1.0 mmol) and HOBt (0.14 g, 1.0 mmol) are dissolved in 12 mL of DMF. DCC (0.206 g, 1 mmol) is added and the resulting solution is stirred under argon for 18 hours at ambient temperature. The mixture is filtered and the filtrate is poured into 200 mL of diethyl ether. The resulting precipitate is collected on a glass frit, washed with ether and dried under suction to provide a white powder.

B. N-[4-(4-guanidinobenzoyloxy)benzoyl]-2-aminoethyl-poly(ethylene glycol) monomethyl ether methanesulfonate salt: The product from step A (0.89 g, 0.18 mmol), 4-guanidinobenzoic acid methane sulfonate salt (0.25 g, 0.89 mmol) and DMAP (0.02 g, 0.15 mmol) are dissolved in 10 mL of DMF. DCC (0.18 g, 0.89 mmol) is added and the resulting solution is stirred under argon for 20 hours. The mixture is filtered and the filtrate is poured into 200 mL of ether. The resulting precipitate is collected on a glass frit, washed with ether, and dried under suction. The resulting white powder is dissolved in warm ethanol (75 mL), filtered, and placed in a refrigerator (4° C.) for 72 hours. The resulting crystals are collected on a glass frit and washed with cold ethanol followed by diethyl ether and dried under suction to give N-[4-(4-guanidinobenzoyloxy)benzoyl]-2-aminoethyl-poly(ethylene glycol) monomethyl ether methanesulfonate salt as a white powder.

EXAMPLE 10

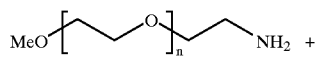

-continued

N-(4-benzamidino)-2-aminoethyl-poly(ethylene glycol) monomethyl ether, hydroiodide salt A. N-(4-cyanobenzoyl)-2-aminoethyl-poly(ethylene glycol) monomethyl ether: 0.1 g (0.02 mmol) of 2-aminoethyl-poly(ethylene glycol)-monomethyl ether ($M_n$~5000) and triethylamine (1.1 eq.) are dissolved in 10 mL of dichloromethane. To the stirring solution under argon is added 4-cyanobenzoyl chloride (1.1 eq.). The solution is stirred for 1 hour and then diluted with cold ether to produce N-(4-cyanobenzoyl)-2-aminoethyl-poly(ethylene glycol) monomethyl ether which is collected by filtration.

B. N-(4-benzamidino)-2-aminoethyl-poly(ethylene glycol) monomethyl ether, hydroiodide salt: The product from step A (0.06 g, 0.012 mmol) is dissolved in 3 mL of pyridine. Triethylamine (0.2 mL) is added. The solution is saturated with hydrogen sulfide gas and is stirred for 18 hours at ambient temperature. The greenish-brown solution is purged with argon and then diluted with 5 mL of dichloromethane. The solution is diluted with ether until a precipitate is observed. The solid is collected and transferred to another reaction vessel in 4 mL of p-dioxane. To the light yellow solution is added 0.2 mL of methyl iodide and the solution is stirred at ambient temperature overnight. The reaction mixture is reconcentrated in vacuo and then redissolved in 3 mL of methanol. Ammonium acetate (0.02 g) is added and the mixture is heated to reflux for 4 hours. The methanol is removed and the residue is treated with cold ether. The resulting N-(4-benzamidino)-2-aminoethyl-poly (ethylene glycol) monomethyl ether, hydroiodide salt is collected.

EXAMPLE 11

Anhydrous cesium carbonate (0.1 g, 0.32 mmol) is added, and the mixture is stirred at ambient temperature for 18 hours. The cloudy solution is filtered and the filtrate is concentrated in vacuo. Ether is added to the resulting solution to produce a yellow precipitate which is collected and washed with ether. The solid is dissolved in dichloromethane (2 mL) and filtered, then poured into ether. The resulting precipitate is collected and washed with 10% iso-propanol in ether followed by ether and then dried under suction. The solid is recrystallized from warm ethanol to give N-(4-cyanophenyloxy)-acetyl-2-aminoethyl-poly (ethylene glycol) monomethyl ether as an off-white powder.

C. N-[4-(aminoiminomethyl)phenyloxy]-acetyl-2-aminoethyl-poly(ethylene glycol) monomethyl ether, hydroiodide salt: The product from step B (0.22 g, 0.04 mmol) is dissolved in a mixture of triethylamine (200 μL) in pyridine (2.0 mL). The solution is saturated with hydrogen sulfide gas and stirred for 18 hours at ambient temperature. The solution is purged with argon and then diluted with dichloromethane (1 mL). The mixture is poured into cold

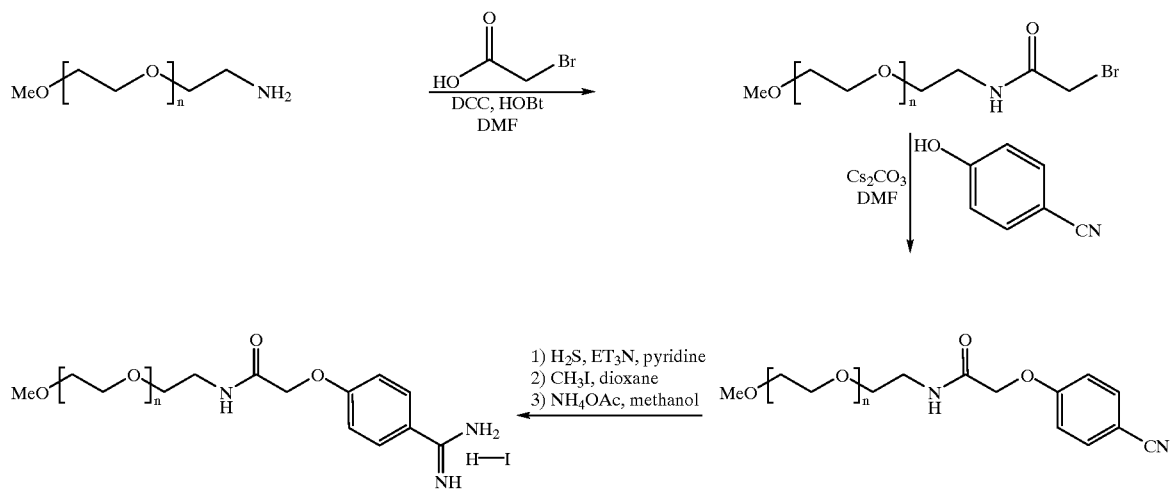

N-[4-(aminoiminomethyl)phenyloxy]-acetyl-2-aminoethyl-poly(ethylene glycol) monomethyl ether, hydroiodide salt A. N-bromoacetyl-2-aminoethyl-poly(ethylene glycol) monomethyl ether: 2-aminoethyl-poly(ethylene glycol) monomethyl ether (0.4 g, 0.08 mmol, $M_n$~5000) and HOBt (0.11 g, 0.8 mmol) are dissolved in dichloromethane (3 mL). Bromoacetic acid (0.11 g, 0.8 mmol) is added, followed by DCC (0.17 g, 0.8 mmol). NMP (0.5 mL) is added, and the mixture is stirred 1 hour at ambient temperature. The mixture is filtered and the filtrate is poured into cold diethyl ether. The resulting N-bromoacetyl-2-aminoethyl-poly (ethylene glycol) monomethyl ether is collected and used without further purification.

B. N-(4-cyanophenyloxy)-acetyl-2-aminoethyl-poly (ethylene glycol) monomethyl ether: The product from step A is placed in a reaction vessel with 4-cyanophenol (0.03 g, 0.24 mmol) and the mixture is dissolved in dry DMF (5 mL).

diethyl ether and the resulting precipitate is collected, washed with ether, and dried under suction. The solid is transferred to a reaction vessel with p-dioxane (2 mL) and methyl iodide (0.2 mL) is added. The mixture is heated under argon to 50° C. for 1.5 hours. The volatiles are removed in vacuo and the residue is dissolved in methanol (2 mL). Ammonium acetate (0.02 g, 0.2 mmol) is added, the mixture is refluxed under argon for 3 hours, cooled to ambient temperature, and stirred overnight. The volatiles are removed in vacuo, and the residue is triturated with 2 mL dichloromethane, filtered, and the filtrate is poured into cold diethyl ether. The resulting precipitate is collected and recrystillized from warm ethanol to give N-[4-(aminoiminomethyl)phenyloxy]-acetyl-2-aminoethyl-poly (ethylene glycol) monomethyl ether, hydroiodide salt, as a white solid.

EXAMPLE 12

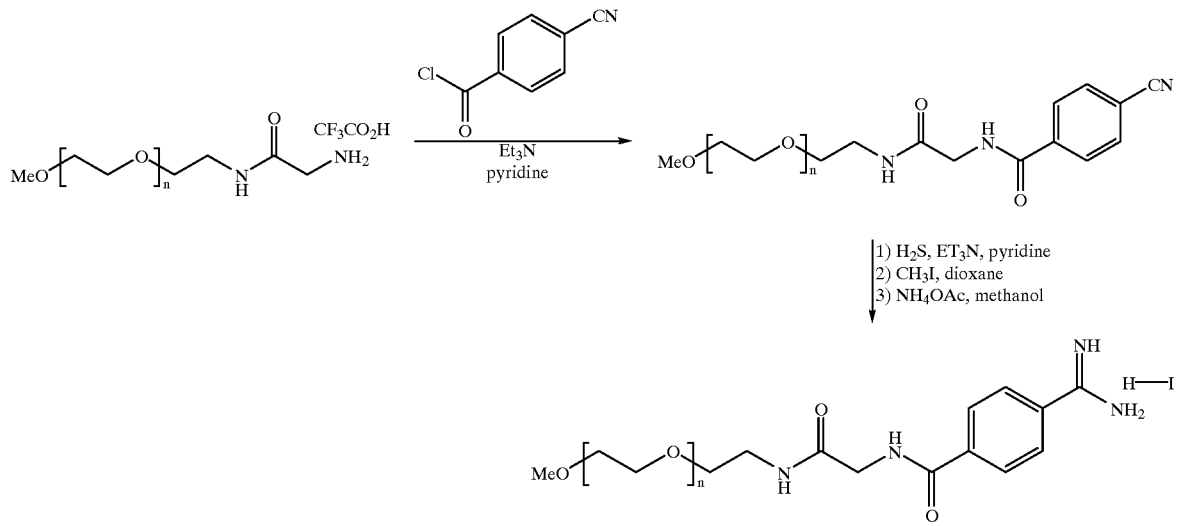

N-[4-(aminoiminomethyl)-benzoyl]-glycyl}-2-aminoethyl-poly(ethylene glycol) monomethyl ether, hydroiodide salt A. [N-(4-cyanobenzoyl)-glycyl]-2-aminoethyl-poly (ethylene glycol) monomethyl ether: N-glycyl-2-aminoethyl-poly(ethylene glycol) monomethyl ether, trifluoroacetate salt, $M_n$~5,000 (0.2 g, 0.04 mmol) and 4-cyanobenzoyl chloride (0.07 g, 0.4 mmol) are dissolved in pyridine (2 mL) and triethylamine (0.2 mL). The solution is stirred for 3 hours at ambient temperature and the volatiles are removed in vacuo. The residue is dissolved in dichloromethane and poured into cold diethyl ether. The resulting precipitate is collected, washed with ether and dried under suction. The solid thus obtained is recrystallized from warm ethanol to give [N-(4-cyanobenzoyl)-glycyl]-2-aminoethyl-poly(ethylene glycol) monomethyl ether.

B. N-[4-(aminoiminomethyl)-benzoyl]-glycyl}-2-aminoethyl-poly(ethylene glycol) monomethyl ether, hydroiodide salt: The product of step A (0.14 g, 0.03 mmol) is dissolved in triethylamine (200 µL) and pyridine (2.0 mL). The solution is saturated with hydrogen sulfide gas and stirred for 18 hours at ambient temperature. The greenish-brown solution is purged with argon and then diluted with 1 mL of methylene chloride. The mixture is poured into cold ether and the resulting precipitate is collected, washed with ether, and dried under suction. The solid is transferred to a reaction vessel with p-dioxane (2 mL) and methyl iodide (0.2 mL) is added. The mixture is heated under argon to 50° C. for 1 hr. The volatiles are removed in vacuo, and the residue is dissolved in methanol (2 mL). Ammonium acetate (0.013 g, 0.17 mmol) is added, and the mixture is refluxed under argon for 3 hours, cooled to ambient temperature and stirred overnight. The volatiles are removed in vacuo, and the residue is triturated with 2 mL dichloromethane, filtered, and the filtrate is poured into cold ether. The resulting precipitate is collected and recrystallized from warm ethanol to give N-[4-(aminoiminomethyl)-benzoyl]-glycyl}-2-aminoethyl-poly(ethylene glycol) monomethyl ether, hydroiodide salt, as a white solid.

EXAMPLE 13

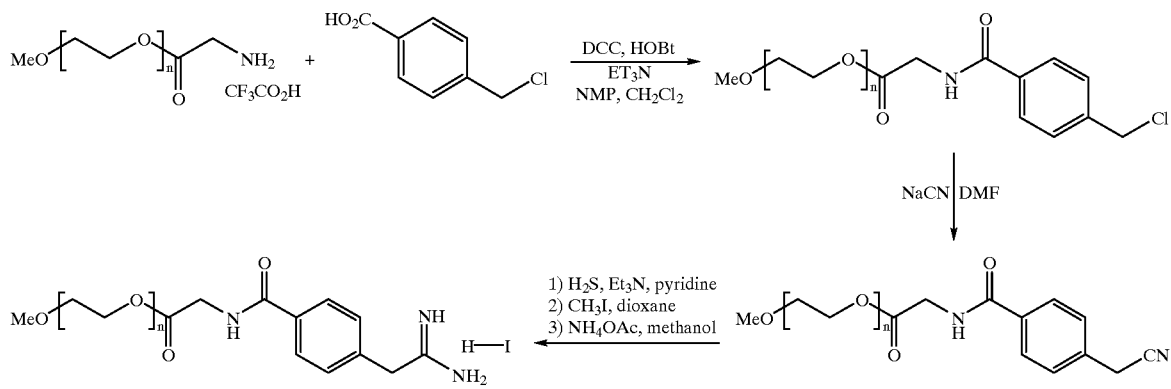

N-[4-(2-amino-2-iminoethyl)-benzoyl]-glycyl-poly (ethylene glycol) monomethyl ether, hydroiodide salt A. N-(4-chloromethylbenzoyl)-glycyl-poly(ethylene glycol) monomethyl ether: Glycyl-(polyethylene glycol) monomethyl ether, trifluoroacetate salt, (0.2 g, 0.04 mmol), HOBt (0.027 g, 0.2 mmol), and 4-chloromethylbenzoic acid (0.034 g, 0.2 mrnol) are dissolved in dichloromethane (2 mL) and NMP (1 mL). DCC (0.04 g, 0.2 mmol) and triethylamine (5.5 µL) are added, and the mixture is stirred for 18 hours at ambient temperature. The solution is filtered and the filtrate is poured into ether. The resulting precipitate is collected, washed with iso-propanol/ether (1:1 v:v), washed with ether and dried under suction to give N-(4-chloromethylbenzoyl)-glycyl-poly(ethylene glycol) monomethyl ether as a white solid.

B. N-(4-cyanomethylbenzoyl)-glycyl-poly(ethylene glycol) monomethyl ether: The product of step A (0.16 g, 0.032 mmol) is dissolved in DMF (5 mL). To this is added sodium cyanide (0.016 g, 0.32 mmol) and the mixture is warmed to 50° C. for 2 hours. The temperature is raised to 100° C. for 30 minutes. The reaction mixture is allowed to cool to ambient temperature and is stirred for 18 hours. The mixture is diluted with dichloromethane (2 mL) and filtered. The filtrate is poured into cold ether and washed with ether, iso-propanol/ether (1: 1 v:v), and then with ether and dried under suction to give N-(4-cyanomethylbenzoyl)-glycyl-poly(ethylene glycol) monomethyl ether as a solid.

C. N-[4-(2-amino-2-iminoethyl)-benzoyl]-glycyl-poly (ethylene glycol) monomethyl ether, hydroiodide salt: The product of step B (0.15 g, 0.03 mmol) is dissolved in a mixture of triethylamine (200 µL) in pyridine (2.0 mL). The solution is saturated with hydrogen sulfide gas and stirred for 18 hours at ambient temperature. The solution is purged with argon and then diluted with 1 mL of dichloromethane. The mixture is poured into cold ether and the resulting precipitate is collected, washed with ether, and dried under suction. The solid is transferred to a reaction vessel containing p-dioxane (2 mL). Iodomethane (0.2 mL) is then added. The mixture is heated under argon to 50° C. for 1 hour. The volatiles are removed in vacuo, and the residue is dissolved in methanol (2 mL). Ammonium acetate (0.014 g, 0.18 mmol) is added, and the mixture is refluxed under argon for 3 hours, cooled to ambient temperature and stirred overnight. The volatiles are removed in vacuo, the residue is triturated with 2 mL dichloromethane, filtered, and the filtrate is poured into cold ether. The resulting Precipitate is collected and recrystallized from warm ethanol to give N-[4-(2-amino-2-iminoethyl)-benzoyl]-glycyl-poly (ethylene glycol) monomethyl ether, hydroiodide salt, as a solid.

EXAMPLE 14

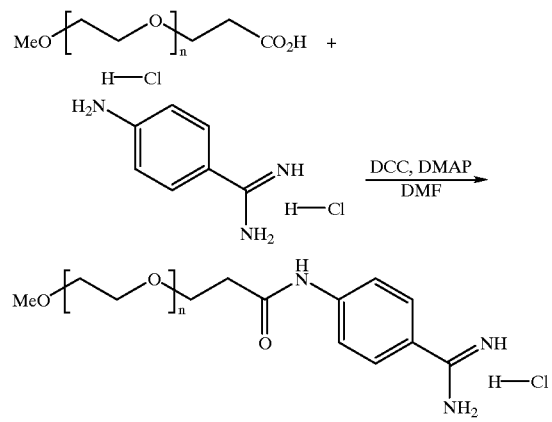

Poly(ethylene glycol)-3-propionic acid monomethyl ether (0.18 g, 0.033 mmol) taken up in DMF (15 mL). p-Aminobenzamidine dihydrochloride (0.08 g, 0.33 mmol), DMAP (0.04 g, 0.33 mnuol) and DCC (0.08 g, 0.33 mmol) are added and the reaction is stirred at ambient temperature overnight. The mixture is filtered and the filtrate is diluted with ether to produce a precipitate. The solid is collected and washed with ether (3x) to produce a hygroscopic solid which is lyopholized to give a powder.

EXAMPLE 15

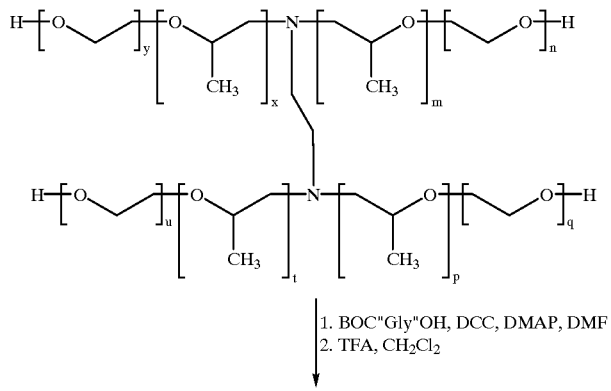

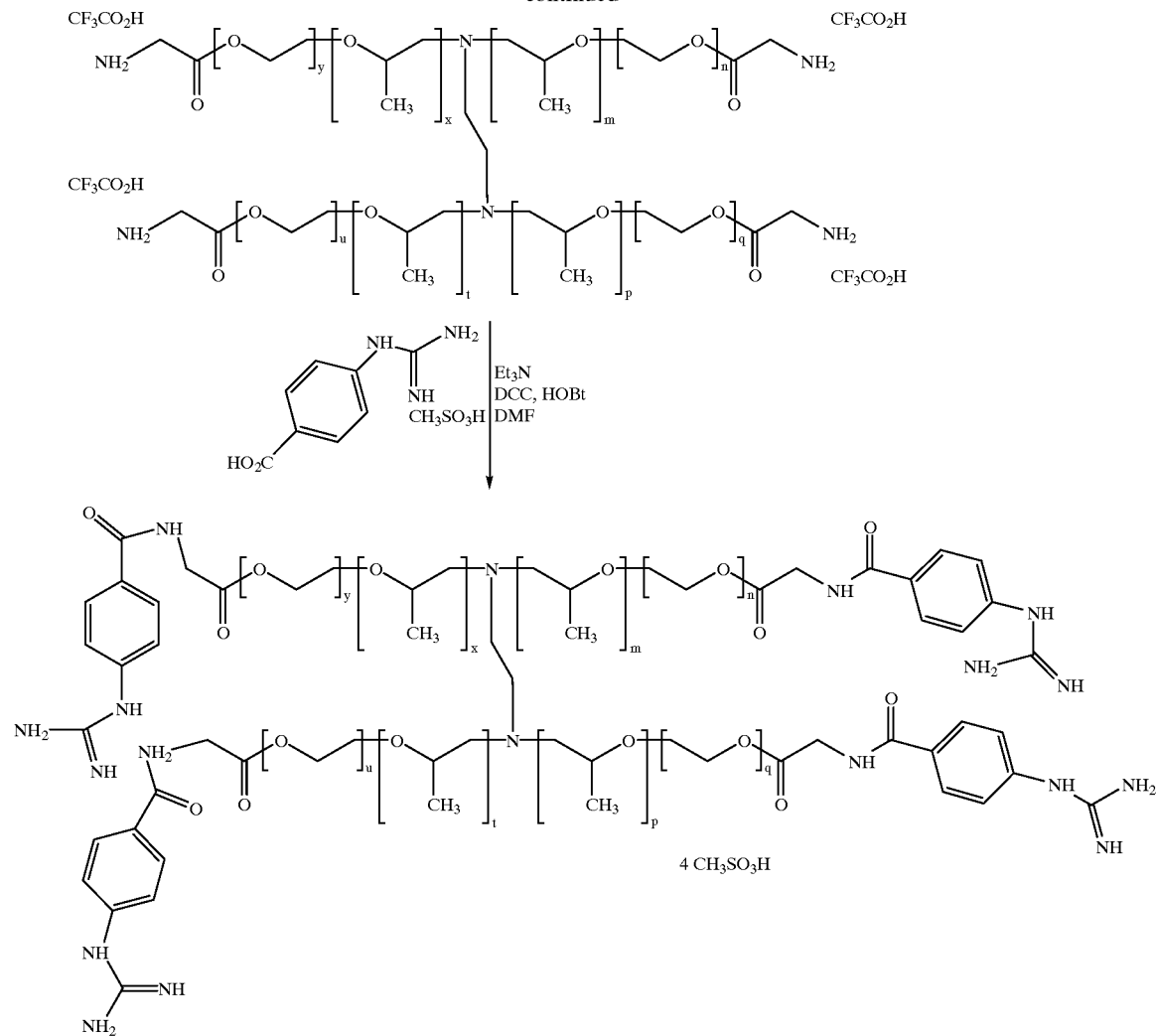

A. Tetronic 908® (BASF) (1 g, 0.04 mmol, $M_n$=25,000 Da), a 4-arm star poly(alkylene oxide) copolymer formed from reaction of propylene oxide with ethylene diamine followed by reaction with ethylene oxide, is weighed into a reaction vessel with N-(tert-butoxycarbonyl)-glycine (0.28 g, 1.6 mmol) and DMAP (0.02 g, 0.16 mmol). The mixture is dissolved in 15 mL DMF, and DCC (0.33 g, 1.6 mmol) is added. After stirring for 24 hours at ambient temperature, the mixture is filtered and the filtrate is poured into cold ether. The precipitate which results is collected on a filter funnel and washed with ether.

B. The product from step A is dissolved in dichloromethane (20 mL) and is treated with trifluoroacetic acid (15 mL) for 1 hour at ambient temperature. The solution is poured into cold ether and thie precipitate which results is collected on a filter funnel, washed with ether and dried under suction.

C. The product from step B (0.79 g, 0.03 mmol) is placed in a reaction vessel with 4-guanidinobenzoic acid methanesulfonate salt (0.18 g, 0.63 mmol) and 1-hydroxybenzotriazole hydrate (HOBt) (0.09 g, 0.64 mmol). The mixture is dissolved in DMF (10 mL) and triethylamine (0.1 mL) is added. After the solids are dissolved DCC (0.13 g, 0.63 mmol) is added and the reaction is stirred overnight at ambient temperature. The reaction mixture is filtered and the filtrate is poured into cold ether. The resulting precipitate is collected, washed with ether and recrystallized from warm ethanol to give the desired product as an off-white powder.

EXAMPLE 16

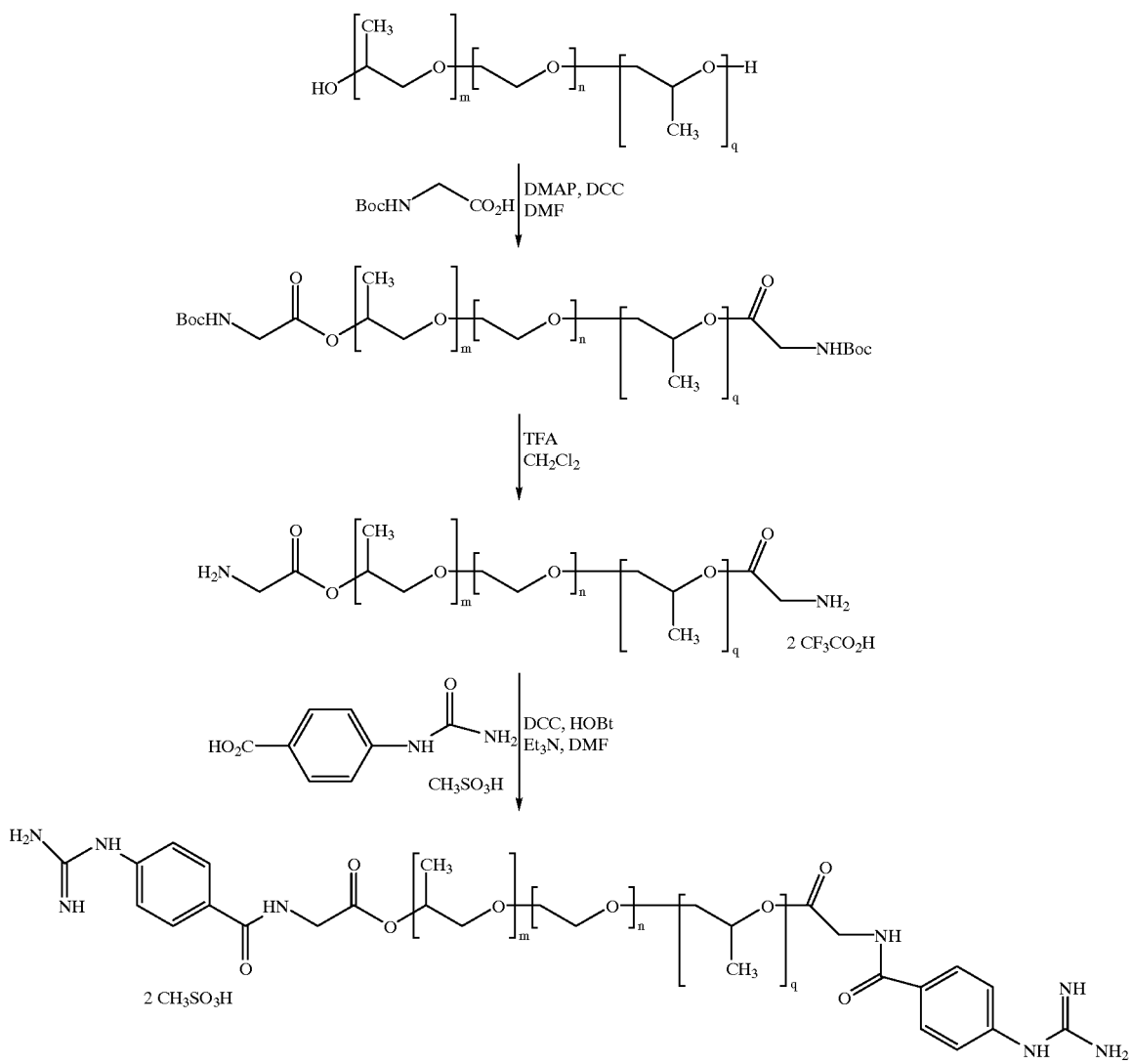

A. Pluronic® 10-R8 (BASF) (1 g, 0.22 mmol, $M_n$~4550) is placed in a reaction vessel with with N-(tert-butoxycarbonyl)-glycine (Boc-glycine) (0.77 g, 4.4 mmol) and DMAP (0.08 g, 0.7 mmol). The solids are dissolved in dry DMF, and DCC (0.91 g, 4.4 mmol) is added and the reaction is stirred overnight at ambient temperature. The resulting mixture is filtered and the filtrate is poured into 200 mL of 1:1 diethyl ether/pentane (v:v). The precipitate which results is collected on a glass frit, washed with additional pentane, dried under suction, and used without further purification.

B. The product of step A (0.75 g, 0.16 mmol) is dissolved in 10 mL of dichloromethane. Trifluoroacetic acid (10 mL) is added, and the solution is stirred for 1 hour at ambient temperature. The solution is poured into 200 mL of 1:1 diethyl ether/pentane (v:v) to produce a white precipitate which is collected on a glass frit, washed with pentane and dried under suction.

C. The product of step B (0.5 g, 0.11 mmol) is placed in a reaction vessel with HOBt (0.3 g, 2.2 mmol), 4-guanidinobenzoic acid methanesulfonate salt (0.61 g, 2.2 mmol), and the mixture is dissolved in dry DMF. DCC (0.45 g, 2.2 mmol) is added, and the reaction is stirred overnight at ambient temperature. The resulting mixture is filtered, and the filtrate is poured into 200 mL of 1:1 diethyl ether/pentane (v:v). The precipitate which results is collected on a glass frit, dissolved in warm ethanol, and cooled to 0° C. to produce a white precipitate. This is collected, washed with pentane and dried under suction.

EXAMPLE 17
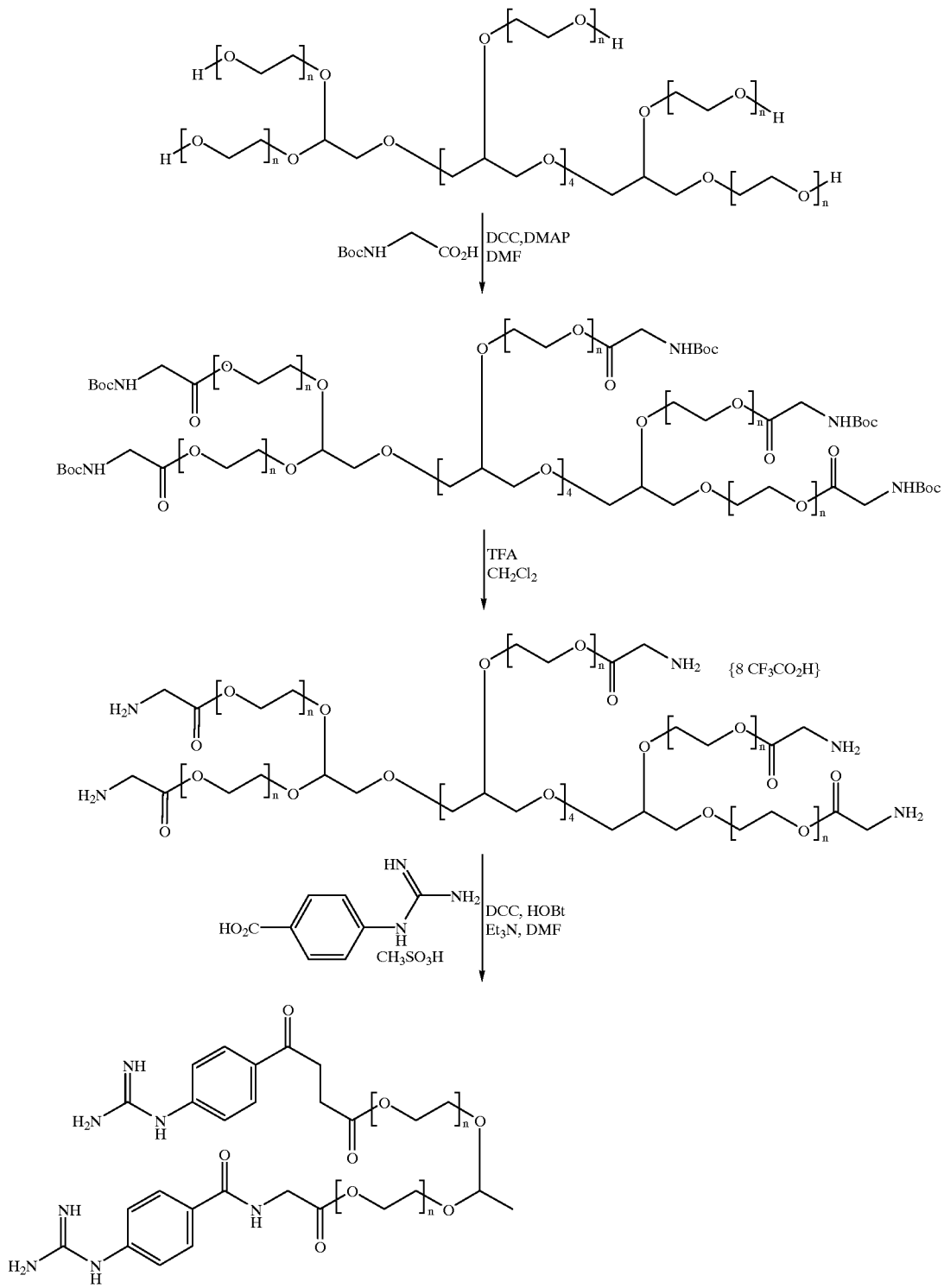

-continued

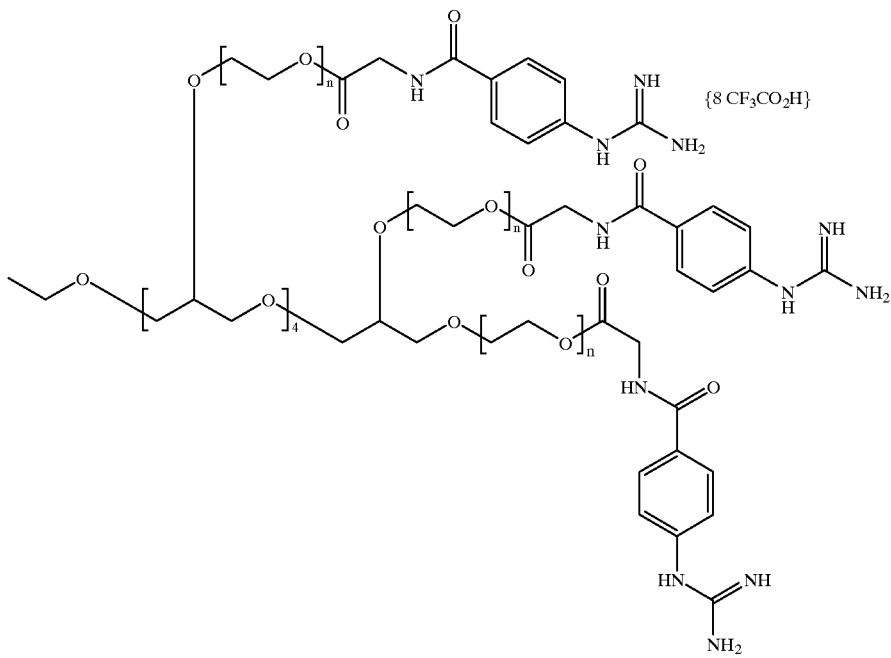

A. The branched poly(ethylene glycol) polymer (1.0 g, 0.1 mmol, $M_n$~10,000), N-(tert-butoxycarbonyl)-glycine (Boc-glycine) (0.7 g, 4.0 mmol), and DMAP (0.49 g, 4.0 mmol) are combined and dissolved in DMF. DCC (0.83 g, 4.0 mmol) is added and the reaction is stirred at ambient temperature for 18 hours under argon. The reaction is filtered and the filtrate is diluted in cold ether until a white precipitate of the octa-N-(tert-butoxycarbonyl)-glycyl-poly (ethylene glycol) star polymer is observed. The solid is collected and dried.

B. The recovered product from step A is dissolved in 50% trifluoroacetic acid (10 mL) in dichloromethane and stirred at ambient temperature for 3 hours. The reaction solution is diluted with cold ether until a precipitate of the octa-glycyl-poly(ethylene glycol) star polymer is observed. The product is collected by filtration as the trifluoroacetate salt.

C. The product from step B (0.5 g 0.05 mmol), 4-guanidinobenzoic acid methanesulfonate salt (1.1 g, 4.0 mmol), triethylamine (1 eq.), and HOBt (0.54 g, 4.0 mmol) are dissolved in DMF (25 mL). To the reaction solution is added DCC (0.83 g, 4.0 mmol) and the solution is stirred at ambient temperature for 18 hours. The reaction is filtered and the filtrate is diluted in cold ether to produce the desired product which is collected on a glass frit, washed with ether and dried.

METHODS OF USING THE PRESENT COMPOUNDS

The compounds, compositions, and methods of the present invention are widely useful in health, skin, hair, oral, beauty, and personal care applications. In addition, the present compounds, compositions, and methods are useful for laundry and cleaning, hard surface cleaning, lawn and garden, and coatings applications where enzyme inhibition may provide benefit for the consumer. Non-limiting examples of conditions against which the present compounds and compositions may be utilized includes, but is not limited to, diaper rash, acne, periodontal disease, and obesity. The compounds also have utility as contraceptives and drug delivery systems. The compounds are inhibitors of enzymes including, but not limited to, lipases, serine proteases, metalloproteases, cysteine proteases, and aspartic proteases. More specifically these enzymes include, for example, lipase, carboxypeptidase A, chymotrypsin, elastase, trypsin, and leucine aminopeptidase. The following compound, composition, and method examples do not limit the invention, but provide guidance to the skilled artisan to use the compounds, compositions, and methods of the invention.

Determination of the specificity of an enzyme inhibitor for a certain enzyme is within the skill of the artisan in that field. Appropriate assays, including both in vitro and in vivo assays which are used to determine inhibition of enzymes, are well known and can be found in the literature. For example, the compounds of the present invention may be screened against, for example, isolated lipase, carboxypeptidase A, chymotrypsin, elastase, trypsin, and leucine aminopeptidase. To provide further guidance, the following are examples of assays designed to measure the inhibitory activity of a compound against enzymes, particularly proteolytic and lipolytic enzymes.

EXAMPLE A

Fecal Protease Inhibition Assay

By way of illustration, to determine the activity of fecal protease inhibiting compounds, the compounds of the present invention may be tested in a standard enzyme assay for protease activity, as follows:

Infant feces are collected in a manner to keep them free from urine contamination and mixed with water to obtain a weight by weight (w/w) mixture (e.g., 1:4 w/w). This mixture is then mixed thoroughly to obtain a homogeneous suspension by homogenization or sonication. The feces are then diluted with a reaction buffer, described below, to obtain a fecal concentration which, when added to a protease substrate, hydrolyzes the substrate over a 5 to 60 minute period. Using such a method, for example, fecal trypsin activity may be determined at pH 8.2 in a 50 nM Tris-HCl buffer with 20 mM $CaCl_2$, containing 0.3 mM of the composition to be tested; fecal chymotrypsin activity at pH 7.6 in a 50 mM Tris-HCl buffer with 20 mM $CaCl_2$, containing 0.05 mM of the composition to be tested; and fecal leucine aminopeptidase activity at pH 7.2 in 50 mM sodium phosphate containing the composition to be tested. To test the efficacy of the compositions, several different concentrations of each putative inhibitory composition are added to duplicate feces-containing reaction buffers, and the inhibition of the enzyme activity is measured. Compounds having an $IC_{50}$ of 100 μM or less are preferred compounds of the invention. More preferred are compounds having an $IC_{50}$ to $IC_{90}$, and most preferably an $IC_{80}$ to $IC_{90}$, of 100 μM or less.

EXAMPLE B

In Vitro Skin Test for Inhibition of IL-1α Production

An in vitro method to determine the efficacy of the compounds of the present invention in preventing the proinflammatory response of the skin to feces and fecal enzymes may be performed as follows:

Human keratinocytes are obtained from epidermal tissue and cultured in serum-free medium in plastic culture vessels containing a nylon mesh surface for a period of time until they are confluent. The mesh surface is then raised to the liquid air interface in order to promote differentiation and formation of multilayered organized layers analogous to those found in vivo, including a well defined stratum comeum barrier. Any cell culture system that promotes the growth and differentiation of keratinocytes, as described, may be employed. A commercially available cell culture system suitable for use is Epiderm® (MatTek Corporation).

Infant feces are collected in a manner to keep them free of urine contamination and diluted with phosphate-buffered saline (PBS) (pH 7.2–7.4). The mixture is then mixed thoroughly to obtain a homogenous suspension by homogenization or sonication. To assay for IL-1α production due to fecal enzyme activity, an aliquot of the homogenate is diluted with PBS and added to the surface of a control culture in a culture vessel. To assay for inhibition of IL-1α production due to protease activity, a predetermined quantity of a putative inhibitor (compound) is added to an otherwise identical diluted aliquot of the homogenate prior to adding it to the surface of a test culture. The cultures are allowed to incubate in a controlled atmosphere. At selected times, the control cultures and inhibitor-treated test cultures, and the underlying culture media are harvested. The culture media are assayed for the presence of IL-1α by known methods. For example, a suitable assay for IL-1α is an enzyme-linked immunoabsorbent method commercially available as Quantikine® from R&D Systems.

The percent reduction in IL-1α production due to the presence of the compound (inhibitor) is calculated as follows:

$$\% \text{Reduction} = \frac{(IL - 1\alpha \text{ from control cultures minus } IL - 1\alpha \text{ from test cultures})}{IL - 1\alpha \text{ from test cultures}}$$

USE OF THE COMPOUNDS OF THE PRESENT INVENTION IN ABSORBENT ARTICLES

As an example, the compounds of the present invention are useful of the prevention and treatment of such conditions as, the inflammation, irritation, and/or skin damage associated with conditions such as, for example, diaper rash.

The compounds of the present invention may be delivered from absorbent articles. As used herein, the term "absorbent article" refers to a device with absorbs and retains body exudates. Examples of absorbent articles include feminine hygiene garments such as sanitary napkins, panty liners, and tampons, diapers, incontinence briefs, diaper holders, training pants, and the like.

Preferably, the compounds of the present invention are delivered from an absorbent article such as a diaper. As used herein, the term "diaper" refers to an absorbent article generally worn by infants and incontinent persons, that is worn about the lower torso of the wearer. In other words, the term "diaper" includes infant diapers, training pants, incontinence briefs, and the like.

Compositions suitable for use in the present invention are described in, for example, U.S. patent applications Ser. Nos. 08/926,532 and 08/926,533, each filed on Sep. 10, 1997, U.S. Pat. No. 5,607,760, issued Mar. 4, 1997, U.S. Pat. No. 5,609,587, issued Mar. 11, 1997, U.S. Pat. No. 5,635,191, issued Jun. 3, 1997, and U.S. Pat. No. 5,643,588, issued Jul. 1, 1997.

In a preferred embodiment, compositions of the present invention comprise a compound of the present invention and a skin care carrier ("carrier"). In addition to its function as a vehicle for delivering an effective concentration of a compound to a wearer's skin, the composition comprising the compound may also comprise ingredients that, for example, reduce the adherence of feces to skin, provide a skin-feces barrier function, or provide other therapeutic benefits to the skin (e.g., improve skin softness, maintain or improve skin health), and the like.

The compounds may be incorporated into the absorbent articles neat, such as in dry powder or particulate form, or incorporated into, for example, an aqueous-based pharmaceutically and dermatologically acceptable composition. By "aqueous" is meant any hydrophilic vehicle including, but not limited to, those containing water, alcohols, polymeric hydrogels, weak bases, metal salts, and/or the like that do not interfere, to any significant degree, with the enzyme inhibitory activity of the compound. The compounds may also be incorporated into a water-in-oil emulsion in a hydrophobic compositions and/or as the aqueous component of an oil-in-water emulsion. Preferably, the composition is not pH buffered and, although the initial pH of the compound/composition may range from about 3.5 to about 9.5, depending on its intended location in the absorbent article, it is preferable that the compound/composition intended for direct contact with the skin have an initial pH no less than 3.5 and no greater than about 7.5, and more preferably from about 6.8 to about 7.4.

When delivered from an absorbent article, the compositions of the present invention comprise a safe and effective amount of a compound of the present invention. When compositions are delivered from an absorbent article, the compositions preferably comprise from about 0.01% to about 20%, more preferably from about 1.0% to about 10%, and most preferably about 10%, by weight, of a compound of the present invention.

It will be recognized that of the numerous materials comprising skin care carriers useful in the compositions delivered to skin in accordance with the invention, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 C.F.R. § 347), which presently include: alantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other useful materials are Category III actives as defamed by the FDA (21 C.F.R. § 347), which presently include: live yeast cell derivatives, aldioxa, aluminum acetate, microporous cellulose, cholecalciferol, colloidal oatmeal, cysteine hydrochloride, dexpanthenol, Peruvian balsam oil, protein hydrolysates, recemic methionine, sodium bicarbonate, Vitamin A, and the like.

Many of the FDA monographed skin care ingredients are currently utilized in commercially available skin care products, such as, for example, A and D® Ointment, Vaseline® Petroleum Jelly, Desitin® Diaper Rash Ointment and Daily Care® Ointment, Gold Bond® Medicated Baby Powder, Aquaphor® Healing Ointment, Baby Magic® Baby Lotion, and Johnson's Ultra Sensitive® Baby Cream. An effective concentration of a compound of the present invention may be incorporated into any of these commercial products as compositions of the present invention and may be, for example, delivered from absorbent articles or applied directly to the skin.

As discussed hereinafter, the compositions useful for transferring the compounds of the present invention to the skin of the wearer preferably, though not necessarily, have a melting profile such that they are relatively immobile and localized on the wearer-contacting surface of the article at ambient temperature, are readily transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the article's wearer-contacting surface, relatively low levels of composition are needed to impart the desired skin care benefits.

In a preferred embodiment, the compositions useful herein are oil solutions or water-in-oil emulsions. However, the composition itself may be solid (i.e., the water phase is trapped within a solid hydrophobic phase) or more often semi-solid at ambient temperatures. By "semi-solid" is meant that the composition can have the appearance of a semi-solid but can be made to flow as the shear rate is increased. This is due to the fact that, while the composition contains primarily solid components, it also includes a liquid component. Preferably, the compositions of the present invention have a zero shear viscosity between about $1.0 \times 10^6$ centipose and about $1.0 \times 10^8$ centipose. More preferably, the zero shear viscosity is between about $5.0 \times 10^6$ centipose and about $5.0 \times 10^7$ centipose. As used herein, the term "zero shear viscosity" refers to a viscosity measured at very low shear rates (e.g., $1.0 \sec^{-1}$) using plate and cone viscometer (a suitable instrument is available from TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at ambient temperature to minimize composition migration. In addition, the compositions preferably have a final melting point above potential "stressful" storage conditions that can be greater than about 45° C. Representative compositions having these melt characteristics are described in detail in U.S. Pat. No. 5,643,588, U.S. Pat. No. 5,607,760, U.S. Pat. No. 5,609,587, and U.S. Pat. No. 5,635,191. Specifically, preferred compositions will have the following melt profile:

| Characteristic | Preferred Range | Most Preferred Range |
| --- | --- | --- |
| % Liquid at Ambient Temperature (20° C.) | 2–50 | 3–25 |
| % Liquid at Body Temperature (37° C.) | 25–95 | 30–95 |
| Final Melting Point (° C.) | ≧38 | ≧45 |

To enhance immobility of preferred compositions, the viscosity of the formulated compositions should be as high as possible to prevent flow within the article to an undesired location. Unfortunately, in some instances, higher viscosities may inhibit transfer of composition to the wearer's skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, and more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a therapeutic and/or skin protective benefit in addition to the benefit derived from the compound being an enzyme inhibitor, a useful active ingredient in the skin care carriers and the resulting compositions is one or more skin protectants or emollients. As used herein, the term "emollient" is a material that protects against wetness or irritation, softens, supplies, coats, lubricates, moisturizes, protects and/or cleanses the skin. It will be recognized that several of the monographed actives listed above are "emollients". In a preferred embodiment, these emollients will have either a plastic or liquid consistency at ambient temperatures, i.e., about 20° C.

Representative emollients useful in the present invention include, but are not limited to, emollients that are petroleum-based, sucrose ester fatty acids, polyethylene glycol and derivatives thereof, humectants, fatty acid ester type, alkyl ethyoxylate type, fatty acid ester ethoxylates, fatty alcohol type, polysiloxane type, propylene glycol and derivatives thereof, glycerine and derivatives thereof, including glyceride, acetoglycerides, and ethoxylated glycerides of $C_{12}$–$C_{28}$ fatty acids, triethylene glycol and derivatives thereof, spermaceti or other waxes, fatty acids, fatty alcohol ethers, particularly those having from about 12 to about 28 carbon atoms in their fatty chain, such as stearic acid, propoxylated fatty alcohols, other fatty esters of polyhydroxy alcohols, lanolin and its derivatives, kaolin and its derivatives, any of the monographed skin care agents listed above, or mixtures of these emollients. Suitable petroleum-based emollients include those hydrocarbons, or mixtures of hydrocarbons, having chain lengths of from about 16 to about 32 carbon atoms. Petroleum-based hydrocarbons having these chain lengths include mineral oil and petrolatum (also known as "mineral wax", "petroleum jelly", and "mineral jelly").

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, iso-propyl laurate, iso-propyl myristate, iso-propyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids, e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

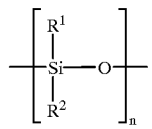

wherein, $R^1$ and $R^2$, for each independent siloxane monomeric unit can each independently be hydrogen or any alkyl, aryl, alkenyl, arylakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanies, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary arylalkyl radicals are benzyl, phenylethyl, phenylethyl, phenylbutyl, tolyl, xylyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotolyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes for use in the present invention are disclosed in U.S. Pat. No. 5,059,282, Ampulski et al., issued Oct. 22, 1991. Particularly preferred polysiloxanes for use as emollients in the compositions of the present invention include phenyl-functional polymethylsiloxanes (e.g., Dow Coming 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; phenyl functional groups are most preferred.

When present, the amount of emollient that can be included in the composition will depend on a variety of factors, including the particular emollient involved, the skin benefits desired, the other components in the composition and like factors. The composition will comprise from 0% to about 99.99%, by total weight, of the emollient. Preferably, the composition will comprise from about 10% to about 95%, more preferably from about 20% to about 80%, and most preferably from about 40% to about 75%, by weight, of the emollient.

Suitable humectants include glycerine, propylene glycol, sorbitol, trihydroxy stearin, and the like.

Another optional, preferred component of the skin care carriers and compositions useful in the present invention is an agent capable of immobilizing the composition (including the compound, the preferred emollient and/or other skin condition/protective agents) in the desired location in or on the treated article. Because certain of the preferred emollients in the composition have a plastic or liquid consistency at 20° C., they tend to flow or migrate, even when subjected to modest shear. When applied to a wearer-contacting surface or other location of an absorbent article, especially in a melted or molten state, the emollient will not remain primarily in or on the treated region. Instead, the emollient will tend to migrate and flow to undesired regions of the article.

Specifically, if the emollient migrates into the interior of the article, it can cause undesired effects on the absorbency of the article due to the hydrophobic characteristics of many of the emollients and other skin conditioning agents used in the compositions useful in the methods of the present invention. It also means that much more emollient needs to be applied to the article to get the desired therapeutic and/or protective benefits. Increasing the level of emollient not only increases the cost, but also exacerbates the undesirable effect on the absorbency of the article's core and undesired transfer of composition during processing/converting of the treated articles.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier), it entraps the emollient on the surface of the article's wearer contacting surface or in the region to which it is applied.

The immobilizing agent counteracts this tendency of the emollient to migrate or flow by keeping the emollient primarily localized on the surface or in the region of the article to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the article's wearer contacting surface or in the region to which it is applied.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the enzyme-inhibiting properties of the compound provide the skin benefits described herein. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behenyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

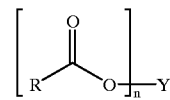

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates, Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927, issued Dec. 29, 1992, Honsa, which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —$CH(CH_2OH)$—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and R is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

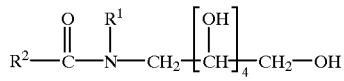

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normnally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch, Inc., West Babylon, N.Y.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

It is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care composition may be utilized, so long as they are applied such that the fluid handling properties of the topsheet are adequately maintained. (For example, as discussed below, nonuniform application of the composition to the topsheet is one means to accomplish this goal). This diminishes the likelihood that body exudates will flow off the composition-treated topsheet rather than being drawn through the topsheet and being absorbed by the absorbent core. Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. Such undesirable effects include reductions in tissue laminate tensile strength, adhesive bond sufficiencies, and the like.

Suitable nonionic surfactants may be substantially non-migratory after the composition is applied to the articles and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in skin care carriers and compositions that will be applied to the articles, at least in the liquid discharge region of the diaper, include alkylglycosides; alkylglycoside ethers as described in U.S. Pat. No. 4,011,389, issued Mar. 8, 1977, Langdon, et al.; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product Of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the skin care carriers and compositions includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25% to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1% to about 50% of the hydrophilic surfactant when needed to increase the wettability properties of the composition. Preferably, the composition comprises from about 1% to about 25%, most preferably from about 10% to about 20%, of the hydrophilic surfactant when needed to increase wettability.

The skin care carriers and resulting compositions of the present invention can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

Wherein water-based skin care carriers and compositions are used, a preservative may be needed. Suitable preservatives include propyl paraben, methyl paraben, benzyl alcohol, benzalkonium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexalene glycol, diol and multi-hydroxy based solvents. Suitable vitamins include A, D-3, E, B-5 and E acetate.

Delivery Systems:

The compounds of the present invention, or the compositions comprising them, may be incorporated into absorbent articles in any delivery system known to those skilled in the art that facilitates contact of an enzyme inhibitor with fecal matter to inhibit enzyme activity therein and/or that facilitates the transfer of a compound or composition to the skin of the wearer of the article to protect against irritation due to fecal enzymes at the skin-feces interface. The delivery system may be a component of any portion or portions of the absorbent article. Such delivery systems include those which deliver the compound neat and those in which the compound is delivered from a vehicle (composition).

The delivery system may include pressure-rupturable or dissolvable microcapsules of "bubbles" containing the compound or a composition comprising the compound. Further, the delivery system may include the compound or a composition comprising the compound in any other form that is activated in the presence of moisture due to urine or other body wastes. Such delivery systems are known to those skilled in the art of absorbent articles.

The delivery system may also provide the compound or composition as a structural component of any of the structures included in the absorbent article. For example, the compounds and compositions of the present invention may be incorporated directly by known methods onto the surface of or within the structure of the topsheet, the backsheet, and/or absorbent core material, or other components of the article during manufacture or assembly, such as by known graft or radical polymerization techniques. The compounds, in powder form, may also be adhered to the surface of absorbent article structures with steam treatment, which produces hydrogen bonding that is easily reversed when such surfaces are wetted by body waste, to release the compound. Regardless of the delivery system employed, the compound or composition may be migratable, meaning it may be physically moved by the flow of urine to other regions in the absorbent article.

The compounds and compositions of the present invention are applied such that during wear, at least some portion of the composition will transfer from the treated article to the wearer's skin. That is, the composition is either applied directly to one or more wearer contacting surfaces, or is applied in alternate locations or means such that the composition is readily available for transfer from one or more wearer contacting surfaces during use without intervention by the user/caregiver. (For example, materials positioned beneath the wearer contacting surface, encapsulated compositions, etc). Suitable methods for applying the compounds or compositions include spraying, printing (e.g., flexographic printing), coating (e.g., contact slot coating, gravure coating), extrusion, or combinations of these application techniques, e.g. spraying the skin care composition on a rotating surface, such as a calender roll, that then transfers the composition to the desired portion of the article. The composition containing the compound can also be applied as a solid material via any of a variety methods, for example, extrusion.

The minimum level of the compound or composition comprising the compound to be applied to the article's wearer-contacting surface is an amount effective for providing the therapeutic, protective and/or skin conditioning benefits when the compound or composition is delivered pursuant to the present invention. The level of compound or composition applied will depend on various factors, including the article component treated, the relative amount of surface area of the wearer-contacting surface not treated with the composition, the composition's content and the like. In order to deliver an effective concentration of the compound to the skin via an absorbent article over time, an effective amount of the composition applied to or migrated to one or more of the wearer-contacting surfaces of the article depends, to a large extent on the particular composition used. The quantity of the composition on at least a portion of the wearer-contacting surface of the absorbent article preferably ranges from about 0.05 mg/in$^2$ (0.0078 mg/cm$^2$) to about 80 mg/in$^2$ (12 mg/cm$^2$), more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). However, these ranges are by way of illustration only and the skilled artisan will recognize that the nature of the composition will dictate the level that must be applied to deliver an effective concentration of the compound and that the desirable level is ascertainable by routine experimentation in light of the present disclosure.

Because the compound or composition is preferably substantially immobilized on the surface of the region treated, relatively small amounts of composition are needed to deliver an effective amount of the compound. It is believed that the ability to use low levels to impart the desired skin benefits is due to the fact that the composition is continuously, automatically delivered as articles are worn. As indicated, the ability to use relatively low levels of skin care composition, allows the article's topsheet to maintain its liquid transfer properties in the liquid discharge region.

The composition can be applied to the article at any point during assembly. For example, the composition can be applied to the finished disposable absorbent product before it has been packaged. The composition can also be applied to a given component (e.g., topsheet, cuffs, sides, waist, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. Since in a preferred embodiment, the composition melts at significantly above ambient temperatures, it is usually applied as a heated composition to the article. Typically, the composition is heated to a temperature in the range from about 35° C. to about 150° C., preferably from about 40° C. to about 100° C., prior to being applied to the article. The compound may be added to the composition prior to or after heating. Once the melted composition has been applied to the article, it is allowed to cool and solidify. Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet after the topsheet is assembled with the other raw materials into a finished product.

EXAMPLE C

Preparation of an Absorbent Article Having a Topsheet Comprising a Composition

A. Preparation of the Composition: A composition (Composition A) is made by mixing the following melted (i.e., liquid) components together: Petrolatum (available from Witco Corp., Greenwich, Conn. as White Protopet®), stearyl alcohol (available from The Procter & Gamble Company, Cincinnati, Ohio as CO1897), aloe extract (available from Madis Botanicals, Inc., South Hackensack, N.J. as Veragel Lipoid in Kaydol), and the compound of Example 5 herein. The weight percentages of these components are shown in Table 1 below:

TABLE 1

| Component | Weight % |
| --- | --- |
| Petrolatum | 52.2 |
| Stearyl Alcohol | 36.9 |
| Aloe | 0.9 |
| Compound of Example 5 | 10.0 |

B. Preparation of a Treated Article by Contact Slot Coating: Composition A is placed into a heated tank operating at a temperature of 170° F. The composition is subsequently applied with a contact applicator (using, for example, a Meltex EP45 hot melt adhesive applicator head having five slots and operating at a temperature of 170° F.) onto the topsheet of an article (commercially available as Pampers® Premium (size 4) Diapers, available from The Procter & Gamble Company, Cincinnati, Ohio) in a striped pattern where the stripes run in the article's longitudinal direction. Specifically, 5 stripes are applied, each stripe measuring 0.25 inches wide (i.e., in the article's lateral direction) and 11.75 inches long at an add-on level=7.7 mg/in$^2$ (12 g/m$^2$, 1.19 mg/cm$^2$). The distance between the stripes is 0.31 inches.

EXAMPLE D

Method of Improving Skin Health

An infant weighing 20 pounds who typically exhibits moderate diaper rash is diapered for a period of 21 days using the diaper of Example C. The infant's diaper is changed according to the routine patterns of the caregiver. (Typical diapering patterns consist of changes every three to four hours during the day and application of a fresh diaper before overnight sleep). No intervention, in the form of manual application of skin protective or moisture repellent products, is performed during this period. During the 21 day period, the infant is observed to have reduced severity of diaper rash.

EXAMPLE E

Method of Improving Skin Health

An active adult incontinent weighing 165 pounds who uses absorbent articles and who persistently has mild skin irritation uses an adult incontinent product analogous to the diaper of Example C for a period of at least five days. The adult's product is changed according to the routine patterns of the user. No intervention, in the form of manual application of skin protective or moisture repellent products, occurs during this period. At the end of the 5 day period, the adult is observed to have reduced or resolved skin irritation.

EXAMPLE F

Method of Maintaining Skin Health

An infant weighing 25 pounds exhibiting no diaper rash is diagnosed with otitis media and is prescribed a course of systemic antibiotics. Based on experience with conventional (untreated) diapers, the caregiver expects that the infant will develop diaper rash resulting from loose stools. As a result, diapers such as that in Example C are used continuously throughout the period of administration of the antibiotic. No intervention, in the form of manual application of skin protective or moisture repellent products, occurs during this period. Throughout the period of antibiotic administration, the subject exhibits no diaper rash.

Use of the Compounds of the Present Invention in Personal Cleansing Compositions The compounds and compositions herein may also be used in any skin care application which is suitable for treatment with an enzyme inhibitor, particularly a proteolytic or lipolytic enzyme inhibitor. Such compositions comprise a safe and effective amount of a compound of the present invention and a personal care carrier.

The compounds and compositions herein can be incorporated into leave-on and rinse-off acne preparations, facial milks and conditioners, shower gels, foaming and non-foaming facial cleansers, cosmetics, hand and body lotions, leave-on facial moisturizers, and cosmetic and cleansing wipes. Of particular interest are those compositions having an anti-acne effect. These products are all manufactured using standard procedures using standard materials known in the art. When used in personal cleansing compositions, the compounds (enzyme inhibitors) are preferably used at levels of greater than about 0.001%, more preferably greater than about 0.01%, and most preferably greater than about 0.1% and at levels preferably less than about 20%, more preferably less than about 10%, and most preferably less than about 5%. Non-limiting examples of personal cleansing compositions are described in the references below, wherein a compound of the present invention may be added to achieve a composition having the desired enzyme inhibiting effect.

Skin Cleansers: U.S. Pat. No. 5,641,479, Linares et al., issued Jun. 24, 1997; U.S. Pat. No. 5,599,549, Wivell et al., issued Feb. 4, 1997; U.S. Pat. No. 5,585,104, Ha et al., issued Dec. 17, 1996; U.S. Pat. No. 5,540,852, Kefauver et al., issued Jul. 30, 1996; and U.S. Pat. No. 5,510,050, Dunbar et al., issued Apr. 23, 1996.

Facial Acne Preparations: U.S. Pat. No. 5,612,324, Guang Lin et al., issued Mar. 18, 1997; U.S. Pat. No. 5,587,176, Warren et al., issued Dec. 24, 1996; U.S. Pat. No. 5,549,888, Venkateswaran, issued Aug. 27, 1996; and U.S. Pat. No. 5,470,884, Corless et al., issued Nov. 28, 1995.

Shower gels: U.S. Pat. No. 5,650,384, Gordon et al., issued Jul. 22, 1997; and U.S. Pat. No. 5,607,678, Moore et al., issued Mar. 4, 1997.

Cosmetics: U.S. Pat. No. 5,641,493, Date et al., issued Jun. 24, 1997; U.S. Pat. No. 5,605,894, Blank et al., issued Feb. 25, 1997; U.S. Pat. No. 5,585,090, Yoshioka et al., issued Dec. 17, 1996.

Hand, Face, and Body Lotions: U.S. Pat. No. 4,939,179, Cheney et al., issued Jul. 3, 1990; and U.S. Pat. No. 5,607,980, McAtee et al., issued Mar. 4, 1997.

Cosmetic and Cleansing Wipes: U.S. Pat. No. 4,045,364, Richter et al., issued Aug. 30, 1977; European Patent Application, EP 0 619 074, Touchet et al., published Oct. 12, 1994; U.S. Pat. No. 4,975,217, Brown-Skrobot et al., issued Dec. 4, 1990; U.S. Pat. No. 5,043,155, Puchalski et al., issued Aug. 27, 1991; and U.S. Pat. No. 5,648,083, Blieszner et al., issued Jul. 15, 1997.

Use of the Compounds of the Present Invention in Pharmaceutical Compositions The compounds and compositions herein may be also be used for the treatment of such conditions as, for example, obesity. Lipase inhibitors have been shown to be useful in the treatment of obesity, acting by partial inhibition of lipase in the intestine. See. e.g., U.S. Pat. No. 5,643,874, Bremer et al., issued Jul. 1, 1997. Accordingly, the compounds of the present invention are useful for such treatment. Of particular benefit of the compounds of the present invention is the decreased absorption of the compounds following oral ingestion due to their polymeric nature.

In addition to the treatment of obesity, the compounds and compositions of the present invention may be used for the treatment and prevention of a wide variety of illnesses or conditions, including those which frequently occur in association with obesity, including but not limited to, diabetes, hypertension, hyperlipidemia, and insulin-resistance syndrome. The compounds and compositions may also be used as actives against periodontal disease and as contraceptives.

The compounds of the present invention can therefore be formulated into pharmaceutical compositions for use in treatment or prophylaxis of conditions such as the foregoing. Standard pharmaceutical formulation techniques are used, such as those disclosed in *Remington's Pharmaceutical Sciences*, Mack Publishing Company, Easton, Pa. (1990).

In addition to the subject compound, the compositions of the subject invention contain a pharmaceutically-acceptable carrier ("carrier"). The term pharmaceutically-acceptable carrier, as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably mammal, being treated.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the compound of the present invention. The amount of carrier employed in conjunction with the compound is sufficient to provide a practical quantity of material for administration per unit dose of the compound. Techniques and compositions for making dosage forms useful in the methods of this invention are described in the following references, all incorporated by reference herein: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, 2d. Edition (1976).

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions of the subject invention may optionally include other drug actives.

Methods of Administration

The compounds and compositions of this invention can be administered topically or systemically. Systemic application includes any method of introducing a compound of the present invention into the tissues of the body, for example, intra-articular, intrathecal, epidural, intramuscular, transdermal, intravenous, intraperitoneal, subcutaneous, sublingual, rectal, and oral administration. When used as pharmaceutical compositions, the compounds of the present invention are preferably administered orally.

The specific dosage of the compound to be administered, as well as the duration of treatment, and whether the treatment is topical or systemic are interdependent. The dosage and treatment regimen will also depend upon such factors as the specific compound used, the treatment indication, the inhibitory activity of the compound, the personal attributes of the subject (such as weight), compliance with the treatment regimen, and the presence and severity of any side effects of the treatment.

Typically, from about 5 mg to about 3000 mg, more preferably from about 5 mg to about 1000 mg, more preferably from about 10 mg to about 100 mg, of a compound of the present invention are administered per day for systemic administration. It is understood that these dosage ranges are by way of example only, and that daily administration can be adjusted depending on the factors listed above.

For localized conditions, topical administration is preferred. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

EXAMPLE G

A tablet for oral administration, according to the present invention, is made comprising:

| Component | Amount |
|---|---|
| Compound of Example 3 | 10 mg |
| Lactose | 120 mg |
| Maize Starch | 70 mg |
| Talc | 4 mg |
| Magnesium Stearate | 1 mg |

Other compounds of the present invention are used with substantially similar results.

What is claimed is:

1. A compound having the structure:

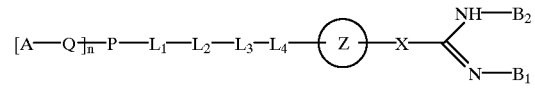

and the tautomers, acceptable salts, and biohydrolyzable amides, ester, and imides thereof, wherein:
(a) $B_1$ is selected from the group consisting of hydrogen, methyl, ethyl, propyl;
(b) $B_2$ is selected from the group consisting of hydrogen, methyl, ethyl, propyl;
(c) X is selected from the group consisting of nil, —$CH_2$—, and —NH—;
(d) Z is an aromatic, substituted or unsubstituted, monocyclic or polycyclic, carbocyclic ring;
(e) $L_1$, $L_2$, and $L_3$ are each, independently, selected from the group consisting of nil, —NH—, —O—, —S—, —C(O)—, —$CF_2$—, alkylene, alkenylene, cycloalkylene, arylene, arylalkylene, arylalkenylene, —C(O)NH—, —$NHSO_2R^1$—, —$C(O)R^2$—, —$C(O)R^3$—O—, —$C(O)R^4$—S—, —$C(O)R^5$—NH—, —NH—$R^6$—, —$OR^7$—, —C(O)O—$R^8$—, —C(O)NH—$R^9$—, —NHC(O)—$R^{10}$—, —OC(O)$R^{11}$— and —C(O)—CH($R^{12}$)—N($R^{13}$)—Y—, wherein $R^1, R^2, R^3, R^4, R^5, R^6, R^7, R^8, R^9, R^{10}$, and $R^{11}$ are, independently selected from the group consisting of alkyl, alkenyl, cycloalkyl, aryl, arylalkyl, arylalkenyl, alkylamino, protected alkylamino, arylamino, protected arylamino, arylalkylamino, protected arylalkylamino, wherein $R^2$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{13}$ is hydrogen, and wherein Y is nil or —C(O)—CH($R^{14}$)—N($R^{15}$)— wherein $R^{14}$ is selected from the group consisting of hydrogen, alkyl, alkenyl, cycloalkyl, aryl, arylalkyl, arylalkenyl, alkylamino, protected alkylamino, arylamino, protected arylamino, arylalkylamino, protected arylalkylamino, and —AA wherein —AA is an amino acid side chain, and $R^{15}$ is hydrogen;

(f) $L_4$ is nil or —C(O)—;

(g) P is a poly(alkylene oxide) polymer selected from the group consisting of a linear poly(alkylene oxide), a branched chain poly(alkylene oxide), and a star poly(alkylene oxide);

(h) n is an integer from 1 to about 100;

(i) Q is nil or —O—; and (j) A is selected from the group consisting of alkyl alkenyl, cycloalkyl, aryl, arylalkyl, arylalkenyl, Z', wherein Z' is an aromatic, substituted or unsubstituted, monocyclic or polycyclic, carbocyclic ring; —C(O)—Z', and —C(O)—$R^{15}$—$CF_3$, wherein $R^{15}$ is nil or alkyl, and

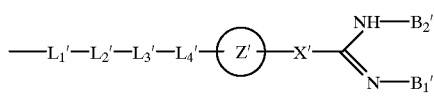

wherein $L_1'$, $L_2'$, $L_3'$, Z', X', $B_1'$, and $B_2'$ are defined as for, respectively $L_1$, $L_2$, $L_3$, Z, X, $B_1$, and $B_2$; wherein the compound is not (I) wherein (I) has the structure:

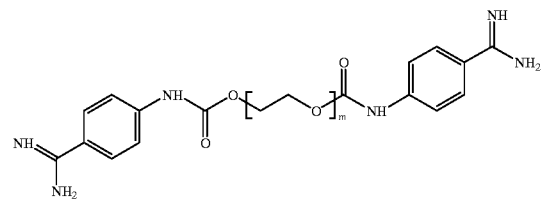

wherein m is an integer from about 5 to about 500.

2. A compound according to claim 1 wherein $B_1$ and $B_2$ are each hydrogen, P is a linear poly(alkylene oxide), and n is 1.

3. A compound according to claim 2 wherein P is $_m$ wherein M is an ethylene oxide monomer, m is an integer from about 5 to about 1000, and Q is —O—.

4. A compound according to claim 3 wherein m is from about 20 to about 500.

5. A compound according to claim 4 wherein X is —NH—.

6. A compound according to claim 5 wherein A is alkyl.

7. A compound according to claim 6 wherein A is methyl.

8. A compound according to claim 7 wherein m is from about 60 to about 200.

9. A compound according to claim 8 selected from the group consisting of:

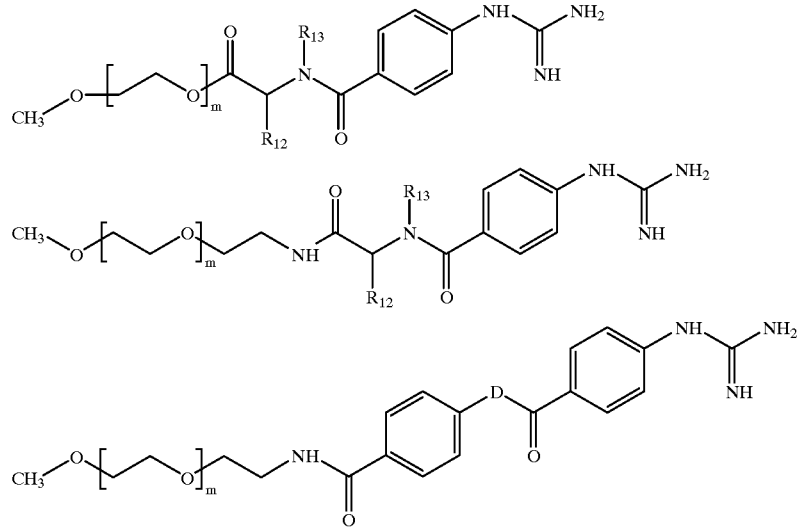

and

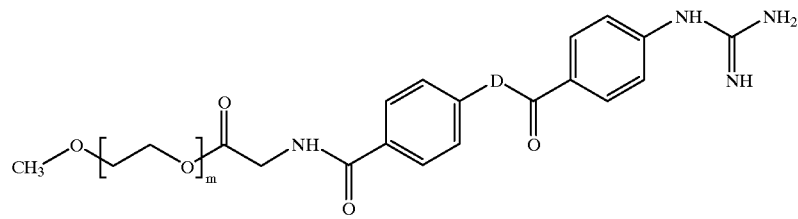

wherein $R^{12}$ is selected from the group consisting of hydrogen, alkyl, cycloalkyl, aryl, arylalkyl, and —AA; $R^{13}$ is hydrogen; and D is selected from the group consisting of —O—, —S—, and —NH—.

10. A compound according to claim 1 wherein Q is —O— and A is

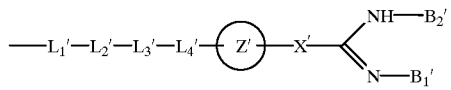

wherein $L_1=L_1'$; $L_2=L_2'$; $L_3=L_3'$; $L_4=L_4'$; $Z=Z'$; $X=X'$; $B_1=B_1'$; and $B_2=B_2'$.

11. A compound according to claim 10 which is:

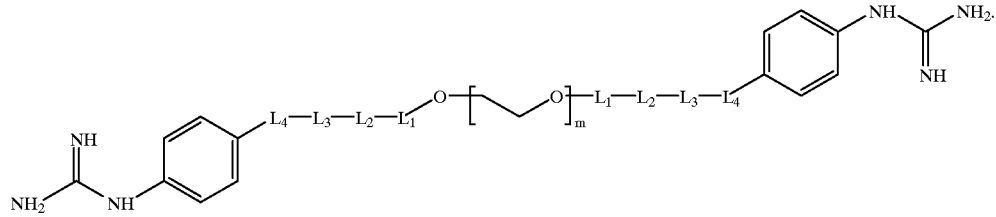

12. A compound according to claim 11 wherein m is from about 60 to about 200.

13. A compound according to claim 12 selected from the group consisting of:

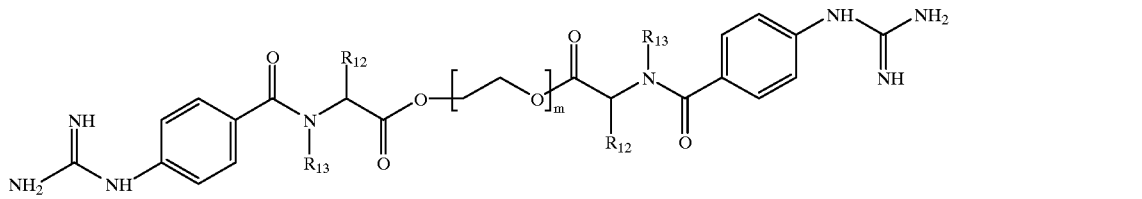

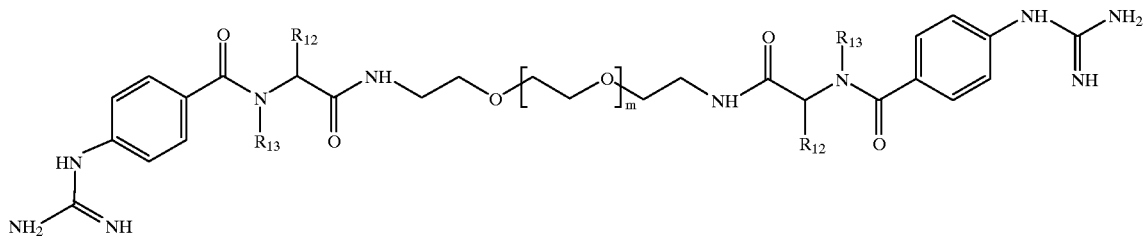

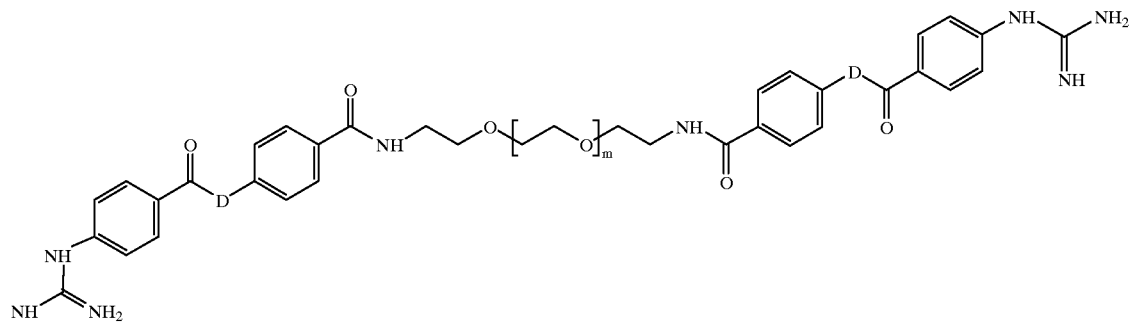

and

-continued

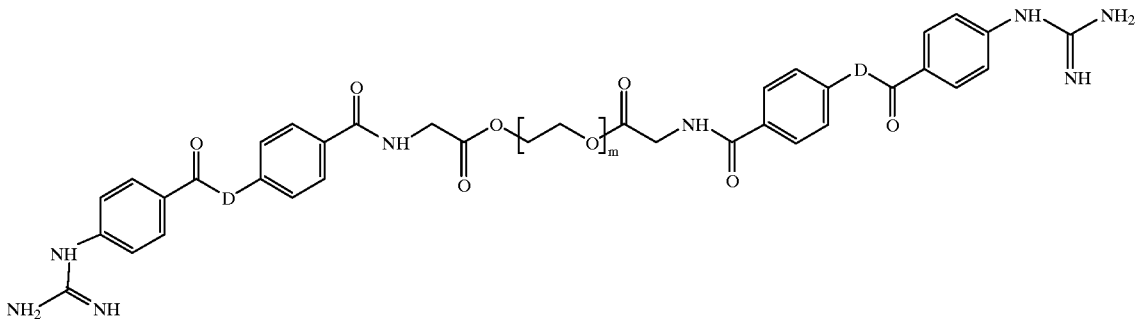

wherein $R^{12}$ is selected from the group consisting of hydrogen, alkyl, cycloalkyl, aryl, arylalkyl, and —AA; and $R^{13}$ is hydrogen, and wherein D is selected from the group consisting of —O—, —S—, and —NH—.

14. A compound according to claim 1 wherein $B_1$ and $B_2$ are each hydrogen and P is a branched chain poly(alkylene) oxide.

15. A compound according to claim 14 wherein P is:

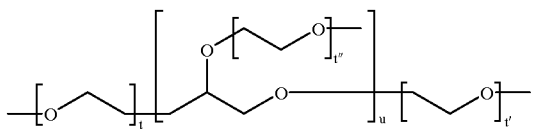

wherein u is an integer from about 1 to about 10 and wherein t, t', and t" are each independently an integer from about 4 to about 990, wherein the compound has the structure:

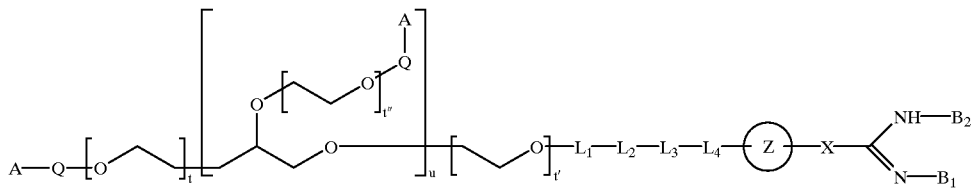

and wherein n is u+1 and Q is nil.

16. A compound according to claim 15 wherein A is:

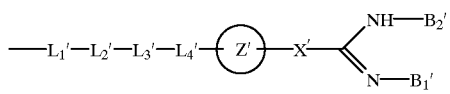

wherein $L_1=L_1'$; $L_2=L_2'$; $L_3=L_3'$; $L_4=L_4'$; $Z=Z'$; $X=X'$; $B_1=B_1'$; and $B_2=B_2'$.

17. A compound according to claim 1 wherein P is a star poly(ethylene oxide) wherein Q is —O— and A is

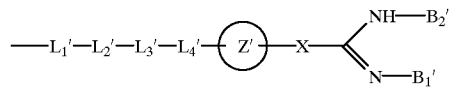

wherein $L_1=L_1'$; $L_2=L_2'$; $L_3=L_3'$; $L_4=L_4'$; $Z=Z'$; $X=X'$; $B_1=B_1'$; and $B_2=B_2'$.

18. A composition comprising:
 (a) a compound according to claim 1; and
 (b) a carrier selected from the group consisting of a skin care carrier, a personal care carrier, and a pharmaceutically-acceptable carrier.

19. A composition according to claim 18 wherein the carrier is a skin care carrier and the composition is deliverable from an absorbent article.

20. A composition comprising:
 (a) a compound according to claim 9; and
 (b) a skin care carrier;
wherein the composition is deliverable from an absorbent article.

21. A composition comprising:
 (a) a compound according to claim 14; and
 (b) a skin care carrier;
wherein the composition is deliverable from an absorbent article.

22. A composition comprising:
 (a) a compound according to claim 17; and
 (b) a skin care carrier;
wherein the composition is deliverable from an absorbent article.

* * * * *

UNITED STATES PATENT AND TRADEMARK OFFICE
CERTIFICATE OF CORRECTION

PATENT NO. : 6,066,673
DATED : May 23, 2000
INVENTOR(S) : John McMillan McIver et al.

It is certified that error appears in the above-identified patent and that said Letters Patent is hereby corrected as shown below:

Column 2, line 25, "comeum" should read -- corneum --.
Column 2, line 28, "comeum" should read -- corneum --.
Column 62, line 31, "Coming" should read -- Corning --.
Column 76, line 60, "$R^2$" should read -- $R^{12}$ --.
Column 78, line 18, "$_m$" should read -- $[M]_m$ --.

Signed and Sealed this

Third Day of April, 2001

Attest:

NICHOLAS P. GODICI

*Attesting Officer*  *Acting Director of the United States Patent and Trademark Office*